(12) United States Patent
Sato et al.

(10) Patent No.: US 10,412,924 B2
(45) Date of Patent: Sep. 17, 2019

(54) YEAR ROUND FLOWERING LUPINE

(71) Applicant: Green Fuse Botanicals, Inc., Santa Monica, CA (US)

(72) Inventors: Kazunori Sato, Tokyo (JP); Tsutomu Semba, Mooka (JP)

(73) Assignee: Green Fuse Botanicals, Inc., Santa Monica, CA (US)

( * ) Notice: Subject to any disclaimer, the term of this patent is extended or adjusted under 35 U.S.C. 154(b) by 0 days.

(21) Appl. No.: 15/476,076

(22) Filed: Mar. 31, 2017

(65) Prior Publication Data

US 2018/0279572 A1    Oct. 4, 2018

(51) Int. Cl.
*A01H 6/54* (2018.01)
*A01H 5/02* (2018.01)

(52) U.S. Cl.
CPC ............. *A01H 6/543* (2018.05); *A01H 5/02* (2013.01)

(58) Field of Classification Search
CPC .................................................... A01H 6/543
See application file for complete search history.

(56) References Cited

PUBLICATIONS

Beuthin (2012, Plant Guide USDA NRCS, Corvallis Plant Materials Ctr., Oregon).*
Puttedrill et al (2004, BioEssays 26(4):363-373).*
Beuthin, M. (2012, Plant Guide for Big Leaf Lupine (*Lupinus polyphyllus*). USDA—Natural Resources Conservation Service, Plant Materials Center, Oregon).*
Puttedrill et al (2004, "It's Time to Flower: The Genetic Control of Flowering Time". BioEssays 26(4):363-373)).*
Shedron et al, HortScience 17(5): 807-809 (Year: 1982).*
Sparks, Brian, Greenhouse Grower Honors 2016 Metal of Excellence Breeding Award Winners, Jul. 12, 2016, online at greenhousegrower.com/author/sparks/ (Year: 2016).*
Dolce, Jasmina, Lawn & Garden Retailer, Demand for Perennials Continues to Rise, Aug. 24, 2016, lgrmag.com/2016/08/demand-for-perennials-continues-to-rise/ (Year: 2016).*
Nelson, M. N., et al., The loss of vernalization requirement in narrow-leafed lupin is associated with a deletion in the promoter and de-repressed expression of a Flowering Locus T (FT) homologue, New Phytologist, 2017, 213: 220-232.

* cited by examiner

*Primary Examiner* — David H Kruse
(74) *Attorney, Agent, or Firm* — Bethany Reid Roahrig; Cochran Freund & Young LLC

(57) ABSTRACT

Lupine plants comprising a homozygous recessive allele that produces a year round flowering characteristic (or year round flowering phenotype or trait) are disclosed. One embodiment relates to the seeds of said year round flowering lupine plants, to the plants of said year round flowering lupine plants, to plant parts of said year round flowering lupine plants, and to methods for producing a lupine plant produced by crossing said year round flowering lupine plant with itself or with another lupine plant. Another embodiment also relates to methods for producing a lupine plant having a year round flowering characteristic (or year round flowering phenotype or trait) and to the year round flowering lupine plants and plant parts produced by those methods. Another embodiment relates to producing interspecific lupine plants having a year round flowering characteristic.

17 Claims, 6 Drawing Sheets

(6 of 6 Drawing Sheet(s) Filed in Color)

Specification includes a Sequence Listing.

YEAR ROUND FLOWERING LUPINE

BACKGROUND

All publications cited in this application are herein incorporated by reference. *Lupinus*, commonly known as lupin or lupine, is a genus of flowering plants in the legume family, Fabaceae. The genus includes over 200 species, including *polyphyllus*, arboreus, *sulphureus*, and *nootkatensis*. *Lupinus* polyphyllus (also known as large-leaved lupine, or, primarily in cultivation, garden lupine) is a species of lupine (lupin) native to western North America from southern Alaska and British Columbia east to Alberta and western Wyoming, and south to Utah and California and commonly grows along streams and creeks, preferring moist habitats.

Lupine can be propagated from seed, cuttings, and tissue culture. Seed, cuttings and tissue culture germination protocols for lupine are well-known in the art.

Lupine is an important and valuable ornamental plant. Thus, a continuing goal of ornamental plant breeders is to develop plants with novel characteristics, such as color, growth habit, and hardiness. To accomplish this goal, the breeder must select and develop plants that have traits that result in superior lupine varieties.

The foregoing examples of the related art and limitations related therewith are intended to be illustrative and not exclusive. Other limitations of the related art will become apparent to those of skill in the art upon a reading of the specification.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

The accompanying figures, which are incorporated herein and form a part of the specification, illustrate some, but not the only or exclusive, example embodiments and/or features. It is intended that the embodiments and figures disclosed herein are to be considered illustrative rather than limiting.

SUMMARY

Figure 1:
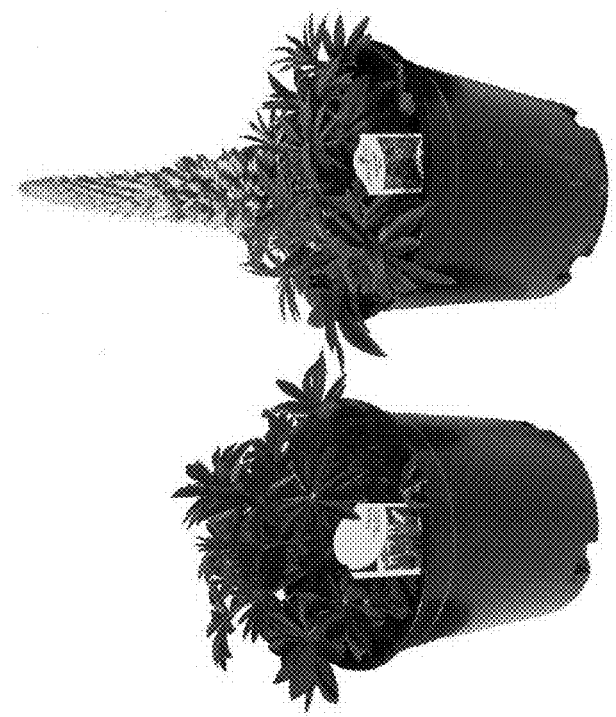
FIG. 1 shows photos taken in March 2017 comparing the plants of Lupine 'The Pages' (left, aerial view), Lupine West Country 'Masterpiece' (a blue bi-color variety) (middle) and Lupine STAIRCASE Blue (right). The plants are all approximately 7 months old.
Figure 1:
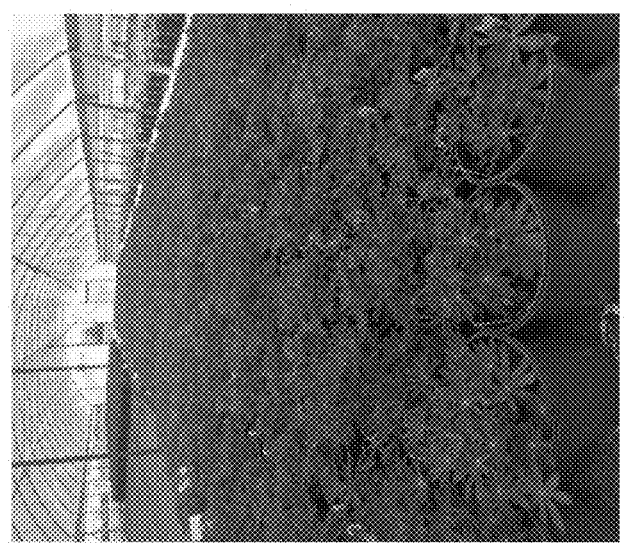

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to one embodiment, there is provided a lupine plant comprising a homozygous recessive YRF allele that produces a year round flowering characteristic, wherein a sample of representative seed of said lupine plant comprising said homozygous recessive YRF allele that produces a year round flowering characteristic is deposited under NCIMB No. 42735. Plants of said lupine are further valued as breeding lines enabling the development of superior ornamental lupine plants having a year round flowering and a range of desirable flower colors and superior growth performance.

Another embodiment discloses a lupine plant comprising a homozygous recessive YRF allele that produces a year round flowering characteristic, wherein said year round flowering characteristic comprises a lupine plant which will flower in days of short and long photoperiods.

Another embodiment discloses a lupine plant comprising a homozygous recessive YRF allele that produces a year round flowering characteristic, wherein said year round flowering characteristic comprises a lupine plant that does not require vernalization or cold temperatures to differentiate flowers.

Another embodiment relates to tissue culture produced from protoplasts or cells from the lupine plants disclosed in the subject application, wherein said cells or protoplasts are produced from a plant part selected from the group consisting of pollen, ovules, embryos, protoplasts, meristematic cells, callus, leaves, anthers, cotyledons, hypocotyl, pistils, roots, root tips, flowers, seeds, petiole, pods, and stems.

In addition to the exemplary aspects and embodiments described above, further aspects and embodiments will become apparent by study of the following descriptions.

DEFINITIONS

In the description and tables herein, a number of terms are used. In order to provide a clear and consistent understanding of the specification and claims, including the scope to be given such terms, the following definitions are provided:

Allele. Allele is any of one or more alternative forms for a gene.

Raceme. As used herein, a "raceme" refers to the flowers and that portion of the peduncle containing the flowers of the plant.

Gene. As used herein, "gene" refers to a segment of nucleic acid.

Long photoperiod. As used herein, refers to a night length of less than 12 hours. Also known as "long-day".

Plant Form. Plant form refers to the silhouette or profile of the plant, ranging from upright to semi-spreading to spreading.

Progeny. As used herein, the descendants of one or more of the parental lines and includes an $F_1$ lupine plant produced from the cross of two lupine plants where at least one plant includes a lupine plant disclosed herein and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

RHS. RHS refers to the acronym for Royal Horticultural Society that publishes a color chart used in the plant industry. All RHS colors referred to herein are from the RHS 2007 edition.

Short photoperiod. As used herein, refers to a night length greater than or equal to 12 hours. Also known as "short-day".

Single Gene Converted (Conversion). Single gene converted (conversion) plants refers to plants which are developed by a plant breeding technique called backcrossing wherein essentially all of the desired morphological and physiological characteristics of a variety are recovered via the backcrossing technique in addition to the single gene transferred into the variety via the initial cross or via genetic engineering.

Vernalization. Vernalization refers to the artificial exposure of plants (or seeds) to low temperatures in order to stimulate flowering.

Year round flowering. As used herein, refers to plants which flower year round when compared with a commercial lupine of the same type and age, and is homozygous recessive for a mutant allele, herein designated YRF, disclosed in this application for plant flowering. Plants comprising the year round flowering trait will flower absent any cold treatment or vernalization, and regardless of day length. Year round flowering lupine are tolerant to USDA zones 3 to 9.

DETAILED DESCRIPTION

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine improved combination of desirable traits from the parental germplasm. These important traits may include flower color, certain plant characteristics, higher vigor, resistance to diseases and insects, better stems and roots, tolerance to drought and heat, and better commercial plant and flower quality.

The present application discloses lupine plants comprising a homozygous recessive mutant allele, YRF, that produces a year round flowering characteristic, wherein said lupine plants will flower in days of short and long photoperiods and do not require cold temperatures or vernalization to flower, wherein a sample of representative seed of the lupine plant comprising said homozygous recessive mutant allele that produces a year round flowering characteristic is deposited under NCIMB No. 42735. Plants of said lupine are further valued as breeding lines enabling the development of superior ornamental lupine plants exhibiting year round flowering and a range of desirable flower colors and superior growth performance.

The novel lupine disclosed in the present application are unique in that they exhibit year round flowering. Specifically, a plant as described herein will flower absent of any cold treatment or vernalization, and/or regardless of day length, while retaining the growth rate and form of commercial lupine varieties. The novel year round flowering lupine disclosed in the present application are stable for a variety of colors and characteristics.

The present application also discloses a lupine plant comprising a homozygous recessive YRF allele that produces a year round flowering characteristic, wherein said plant will flower absent of any cold treatment or vernalization, and regardless of day length, wherein a sample of representative seed of the lupine plant comprising said homozygous recessive allele is deposited under NCIMB No. 42735.

The year round flowering lupine disclosed in the present application have shown uniformity and stability, as described in the following section. The year round flowering lupine disclosed in the present application have been asexually and sexually reproduced a sufficient number of generations with careful attention to uniformity of plant type and has been increased with continued observation for uniformity.

Origin of Russell Hybrid Lupine

Commercial Russell hybrid lupine, *Lupinus polyphyllus* hybrid, were thought to be brought from North America to Britain in the 1820's. Russell hybrids, *Lupinus russellii* hort, were bred because *Lupinus polyphyllus* originally were of basic colors, white pink to purple-blue flowers, and had large gaps in the flowering raceme. Please see United States Department of Agriculture, "Big Leaf Lupine", published October 2012. Over the decades, Russell hybrid plants were selected having denser racemes and more colors than the original *Lupinus* polyphyllus.

Seedlings of *Lupinus* polyphyllus hybrid (Russel's strains) have historically had both the requirements of vernalization and long photoperiods to develop flowers and be presentable for plant sales to the public. For this reason, *Lupinus* polyphyllus hybrid (Russel's strains) are planted in early summer (or at least by the end of summer) to allow plants to become large and established, so they can survive exposure to low winter temperatures to receive the needed effects of vernalization to flower the next year. *Lupinus* polyphyllus hybrid (Russel's strains) are over-wintered in containers protected only from the most severe temperatures and then allowed to naturally flower in late spring or early summer with lengthening photoperiods. Unless *Lupines polyphyllus* hybrid (Russel's strains) are vernalized, they will not predictably flower uniformly across a crop even when they are exposed to the long days of the late spring and summer.

Examples

1. Development and Discovery of Lupine Plants Having a Year Round Flowering Characteristic The development of the year round flowering lupine disclosed in the present application resulted from a breeding program to develop Russell Lupine plants that would bloom with a shortened photoperiod and without vernalization. Working within breeding populations that flowered typical to Russel *Lupines*, an individual plant was identified in early 2009 which flowered very early compared to other plants in the population. The plant was named 'Very Early Flower'.

In April 2009, the individual plant was crossed with other sibling clones that had different flower colors. Five to 10 seeds were harvested from each crossing in July 2009. Those seeds were subsequently sown in September 2009 for testing in the following year. Additionally, it was observed that 'Very Early Flower' kept flowering for a longer period into the summer. This second attribute showed that the plant was not only early flowering, but also would generate new reproductive growth that did not require cold treatment or vernalization to flower.

Determination of Genetic Mechanism and Inheritance of Year Round Flowering Lupine Plant Characteristic In March 2010, the flowering of the $F_1$ generation confirmed that the character was of recessive inheritance as none of the $F_1$ plants showed the long flowering trait of the parental line identified in early 2009. Plants from this $F_1$ population were selected for self-pollination and approximately 200 seeds were harvested in July 2010.

In March 2011, approximately 50 (or 25%) of the $F_2$ plants flowered with greenhouse night temperatures maintained at greater than 10° C. This confirmed that the year round flowering characteristic had been inherited and that it was a recessive trait. Additionally, the phenotypes were stable and further, since the trait was found in plants with different flower colors, it is not influenced by flower color.

During the summer of 2012, the breeder took 6 selections and grew them in 18 cm pots on the balcony of his residence in Tokyo, where summer night temperatures reached 23° C. (see Table 1 below). He observed that the plants continued to flower into July 2012, which is much longer than typical lupine strains which finish flowering by late May in Japan due to rapidly increasing nightly temperatures.

TABLE 1

Temperatures in Tokyo, Japan, July 2012

| Temperature | Maximum | Mean | Minimum |
| --- | --- | --- | --- |
| Daily high | 95° F. (31.5° C.) | 83° F. (25.5° C.) | 71° F. (19.5° C.) |
| Daily mean | 86° F. (27° C.) | 78° F. (23° C.) | 68° F. (18° C.) |
| Daily low | 78° F. (23° C.) | 73° F. (20.5° C.) | 64° F. (16° C.) |

The breeder also observed that the plants grown on his balcony produced as many as 12 flower racemes per plant, far exceeding the typical 6 raceme count usually observed for other lupine plants (for example, 'Minaretto') over a growing season.

In February 2013 the breeders achieved very early lines in many flower colors and plant heights (tall and dwarf) from the $F_3$ generation and worked on further generations by sibling mating to maintain hybrid plant vigor and improve the flower color purity.

The lines have continued through the $F_6$ generation in both standard and dwarf heights and many colors. The year round flowering trait is stable and not significantly influenced by photoperiod. $F_6$ seedlings started to flower in January, which allowed for further selections in March 2016. In these selected lines there was no requirement for low temperatures nor long days to initiate flower buds. Year round flowering *Lupinus* polyphyllus hybrid (Russel's strains) can be grown similarly to annuals, a significant production benefit.

Through breeding and laboratory techniques well-known in the art, year round flowering lupine plants can be produced as a homozygous tetraploid or diploid. Additionally, the year round flowering trait can be transferred stably and predictably across different lupine species, different colors, and different genetic backgrounds.

2. Characteristics of Year Round Flowering Lupine Plants

FIGS. 1 to 5 show the botanical characteristics of year round flowering lupine plants *Lupinus* polyphyllus hybrid (Russel strains) STAIRCASE and KELPIE series as compared to *Lupinus* polyphyllus hybrid (Russel strains) 'The Pages', Russell West Country series, and Gallery series, of different colors. The year round flowering plants and West Country plants were grown from tissue culture in Ft. Collins, Colo. The plants were deflasked the second week of August 2016 and placed into 72 unit liner trays. Gallery series plants and 'The Pages' were started from seed in 98 unit liner trays the last week of July 2016 at the same facility in Ft. Collins, Colo. Liners were transplanted 7 to 10 weeks later into 1 gallon containers for seed propagated plants and 2 gallon containers for tissue cultured plants and grown in a greenhouse. No additional cold treatment for vernalization was given and no plant growth regulators were used. No artificial light was used and irrigation was done by hand-watering. Photographs were taken in March 2017 when the plants were approximately 7 months old.

Shown in FIG. 1 is a comparison between *Lupinus* polyphyllus hybrid (Russel strains) 'The Pages' (left, aerial view), lupine West Country 'Masterpiece' (middle), and lupine STAIRCASE Blue (right). STAIRCASE Blue has the year round flowering trait and exhibits early flower initiation before flowers develop on the other plants.

Figure 2:
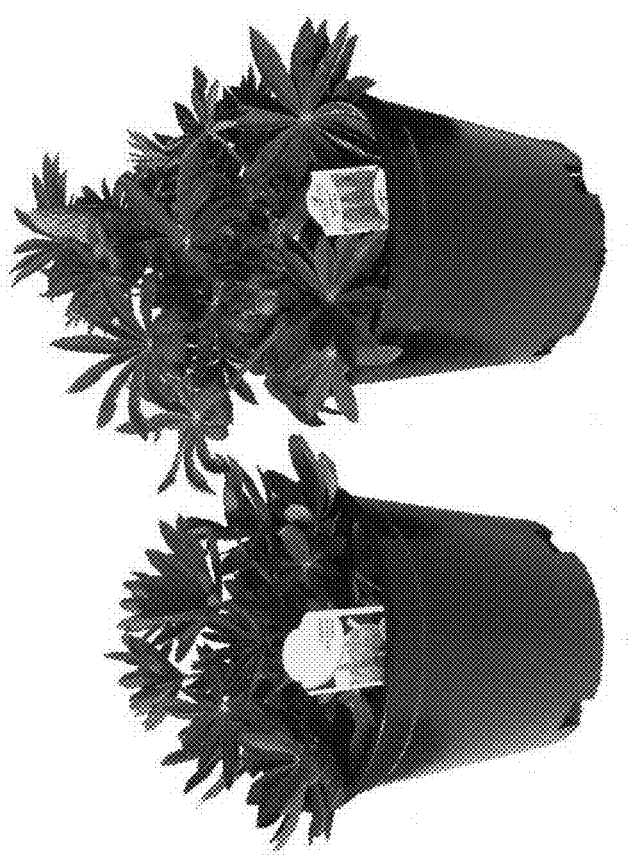
FIG. 2 shows photos taken in March 2017 comparing the plants of Lupine Gallery White and Yellow (left, aerial view), Lupine West Country 'Gladiator' (an orange variety) (middle) and Lupine STAIRCASE Dupline Orange (right). The plants are all approximately 7 months old.
Figure 2:
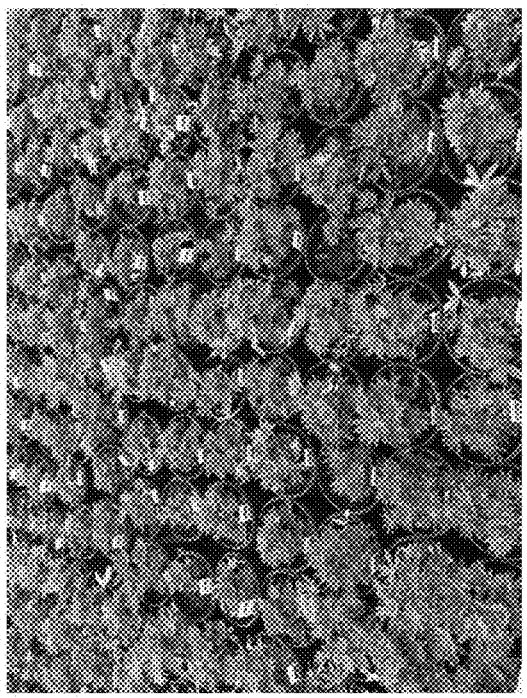

Shown in FIG. 2 is a comparison between lupine Gallery White and Gallery Yellow (left, aerial view), lupine West Country 'Gladiator' (middle), and lupine STAIRCASE Dupline Orange (right). STAIRCASE Dupline Orange has the year round flowering trait and exhibits early flower initiation before flowers develop on the other plants.

Figure 3:
FIG. 3 shows photos taken in March 2017 comparing the plants of Lupine Gallery Red (left, aerial view) Lupine West Country 'Red Rum' (a red variety) (middle) and Lupine STAIRCASE Red (right). The plants are all approximately 7 months old.
Figure 3:
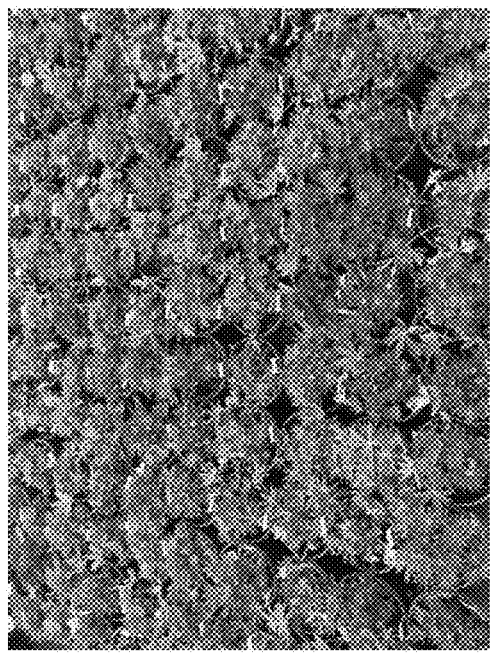

Shown in FIG. 3 is a comparison between lupine Gallery Red (left, aerial view), lupine West Country 'Red Rum' (middle), and lupine STAIRCASE Red (right). STAIRCASE Red has the year round flowering trait and exhibits early flower initiation before flowers develop on the other plants.

Figure 4:
FIG. 4 is a photo taken in March 2017 comparing the plants of Lupine West Country (background beginning at blue arrow) and Lupine STAIRCASE varieties (foreground). The plants are approximately 7 months old.

FIG. 4 shows an aerial view of lupine West Country strains (background beginning at blue arrow), and lupine STAIRCASE strains (foreground). The STAIRCASE series plants have the year round flowering trait and exhibit heavy flower initiation, while the West Country strains do not show any flower development.

Figure 5:
FIG. 5 shows photos taken in March 2017 of the plants of Lupine STAIRCASE Red (left), a tall variety having the year round flowering characteristic, and Lupine KELPIE Dupline Red (right), a dwarf variety having the year round flowering characteristic. The plants are approximately 7 months old.

FIG. 5 shows lupine STAIRCASE Red (left), a tall variety, and lupine KELPIE Dupline Red (right), also known as 'LMIRW01-0', a dwarf variety. Both plants exhibit the year round flowering trait.

Figure 6:
FIG. 6 is a photo taken in October 2016 showing plants of the STAIRCASE series grown in Santa Paula, Calif. The plants are approximately 13 weeks old.

FIG. 6 shows the botanical characteristics of year round flowering lupine plants *Lupinus* sp. (Russel strains) STAIRCASE series grown from tissue culture in Santa Paula, Calif. The plants were deflasked the week of Jul. 4, 2016 and placed into plug trays in a greenhouse. Seedlings of were transplanted into 15 cm, 6 inch pots the third week of August, 2016 and grown in a greenhouse. No plant growth regulators were used. No artificial light was used and irrigation was done by hand-watering. No additional cold treatment for vernalization was given and 2016 was the hottest summer in California history. Photographs were taken the second week of November, 2016 when the plants were approximately 17 weeks old. The plants developed flowers without cold temperatures or vernalization.

3. Crosses of Year Round Flowering Lupine with Other Lupine—Interspecific Crosses of Lupine As shown by the breeding history and data, the year round flowering lupine characteristic is a heritable trait and can be bred into other lupine plants. When in the homozygous form, lupine plants will exhibit the year round flowering phenotype. Interspecific crosses in lupine are well-known in the art. Please see Bragdo, Marie, "Interspecific Crosses in *Lupinus* Cytology and Inheritance in Flower Color", Hereditas, 43 (2): 338-356, July 1957.

For example, a year round flowering *Lupinus* polyphyllus hybrid plant homozygous recessive for the mutant allele YRF, wherein a representative sample of seed containing said allele was deposited under NCIMB No. 42735, may be bred with other *Lupinus* species such as *polyphyllus*, *arboreus*, *sulphureus*, and *nootkatensis* to produce interspecific hybrid seed and progeny *Lupinus* hybrid plants.

4. Botanical Characteristics of Year Round Flowering Lupine

In the following description, color references are made to the Royal Horticultural Society Colour Chart 2007 except where general terms of ordinary dictionary significance are used. The following observations and measurements describe plants grown outdoors in Santa Paula, Calif. Plants were approximately 1 year old, grown in either a 2 gallon or 14 cm nursery container. Measurements and numerical values represent averages of typical plant types.

Table 2 below lists some of the additional botanical characteristics of 'LMIBW03-0', also known as KELPIE 'Blue White', 'LMIRE05-0', also known as KELPIE 'Red', and 'LMIYE06-0', also known as KELPIE 'Yellow'. These dwarf lines all exhibit the year round flowering characteristic, meaning they will flower absent of any cold treatment or vernalization, and/or regardless of day length, and are tolerant to USDA zones 3 to 9. They are compact, herbaceous vigorous perennials with a mounding foliar base topped with upright raceme inflorescences. The plant height to the top of the flowering plane for these dwarf lines does not exceed 35.0 cm. The leaves emerge directly from the base of the plant, or infrequently occur directly on the flowering stem. The leaves are orbicular shaped and palmately compound, occurring mainly as basal whorls, or infrequently alternate along the flowering stem. The inflorescence consists of single, large, papilonaceous flowers evenly and symmetrically arranged on racemes, with individual flowers lasting approximately 15 days.

TABLE 2

Botanical characteristics of dwarf varieties 'LMIBW03-0', 'LMIRE05-0', and 'LMIYE06-0'

| | 'LMIBW03-0' | 'LMIRE05-0' | 'LMIYE06-0' |
|---|---|---|---|
| Spread | Approximately 15 cm to 20 cm | Approximately 25 cm | Approximately 15 cm to 20 cm |
| Leaf length | Range 4.5 cm to 6.0 cm | 7.0 cm | 6 cm to 9.0 cm |
| Leaf diameter | Range 4.5 cm to 6.0 cm | 7.0 cm | 9.0 cm |
| Leaf quantity | Approximately 15 to 20 basal leaves, per plant. Average range 2 to 4 floral stem leaves, per stem | Approximately 10 to 15 basal leaves, per plant. Average range 2 to 4 floral stem leaves, per stem | Approximately 15 basal leaves, per plant. Average range 2 to 4 floral stem leaves, per stem |
| Leaflets quantity | Average 11 | Average 11 | Average 11 |
| Leaflets shape | Oblanceolate | Oblanceolate | Oblanceolate |
| Leaflets arrangement | Radial | Radial | Radial |
| Leaflets length | Longest leaflet per leaf average 3.0 cm to 5.5 cm; Shortest leaflet per leaf average 2.8 cm | Longest leaflet per leaf average 3.5 cm; Shortest leaflet per leaf average 2.5 cm | Longest leaflet per leaf average 3.5 cm to 4.5 cm; Shortest leaflet per leaf average 2.5 cm to 3.3 cm |
| Leaflets width | Central leaflet average 1.6 cm | Central leaflet average 1.6 cm | Central leaflet average 1.5 cm |
| Leaflets apex | Acute to nearly acuminate | Acute to nearly acuminate | Acute to nearly acuminate |
| Leaflets base | Attenuate | Attenuate | Attenuate |
| Leaflets margin | Entire | Entire | Entire |
| Leaflets texture, both surfaces | Glabrous | Glabrous | Glabrous |
| Leaflets appearance, both surfaces | Matte | Matte | Matte |
| Leaflets aspect | Flat to very slightly reflexed downward | Flat to very slightly reflexed downward | Flat to very slightly reflexed downward |
| Leaflets color, upper surface | Near RHS Green 141B | Near RHS Green 137A | Near RHS Green 141B |
| Leaflets color, lower surface | Near RHS Green 141C | Near RHS Green 137D | Near RHS Green 137D |
| Venation type | Pinnate | Pinnate | Pinnate |
| Venation color, upper surface | Near RHS Yellow-Green 145B | Near RHS Yellow-Green 145A | Near RHS Yellow-Green 145A |
| Venation color, lower surface | Near RHS Yellow-Green 144D | Near RHS Yellow-Green 145A | Near RHS Yellow-Green 145C |
| Petiole length | Range 5.0 cm to 9.0 cm | Range 4.0 cm to 11.0 cm | Range 4.0 cm to 7.0 cm |
| Petiole diameter | 0.5 cm | 0.6 cm | 0.4 cm |
| Petiole color | Near RHS Yellow-Green 144C | Near RHS Yellow-Green 144D | Near RHS Yellow-Green 145C |
| Petiole texture | Minutely hirsute | Minutely hirsute | Minutely hirsute |
| Quantity of flowers | 40 to 70 flowers and buds per inflorescence. Typically 1 to 3 inflorescences per plant at one time | 40 to 80 flowers and buds per inflorescence. Typically 1 to 3 inflorescences per plant at one time | 40 to 60 flowers and buds per inflorescence. Typically 1 to 3 inflorescences per plant at one time |

TABLE 2-continued

Botanical characteristics of dwarf varieties 'LMIBW03-0', 'LMIRE05-0', and 'LMIYE06-0'

| | 'LMIBW03-0' | 'LMIRE05-0' | 'LMIYE06-0' |
|---|---|---|---|
| Inflorescence diameter | Approximately 5.0 cm | Approximately 5.0 cm | Approximately 5.0 cm |
| Inflorescence height | Range 8 cm to 15 cm | Range 10 cm to 20 cm | Range 10 cm to 18 cm |
| Flower length (excluding pedicel) | Approximately 2.2 cm | Approximately 1.1 cm | Approximately 1.4 cm |
| Flower height (excluding pedicel) | Average 1.8 cm | Average 1.0 cm | Average 1.0 cm |
| Peduncle length | Approximately 3.0 cm from uppermost leaf to lowermost flower | Approximately 3.0 cm from uppermost leaf to lowermost flower | Approximately 3.0 cm from uppermost leaf to lowermost flower |
| Peduncle diameter | Approximately 0.8 cm | Approximately 0.9 cm | Approximately 0.8 cm |
| Peduncle color | Near RHS Yellow-Green 145A | Near RHS Yellow-Green 145A, flushed RHS Greyed-Purple 187D | Near RHS Yellow-Green 145B |
| Peduncle strength | Flexible, very strong | Flexible, very strong | Flexible, very strong |
| Peduncle texture | Short pubescence | Short pubescence | Slight pubescence |
| Pedicel length | Approximately 1.1 cm | Approximately 1.0 cm | Approximately 0.8 cm |
| Pedicel diameter | Approximately 0.2 cm | Approximately 0.2 cm | Approximately 0.2 cm |
| Pedicel color | Near RHS Yellow-Green 145C flushed Greyed-Red 181C, or colored entirely 181D | Near RHS Greyed-Purple 186B | Near RHS Yellow-Green 145B |
| Pedicel strength | Strong | Strong | Strong |
| Pedicel texture | Softly pubescent | Softly pubescent | Slightly pubescent |
| Petal quantity and arrangement | 1 upper banner, 2 lateral "wings" and a lower keel | 1 upper banner, 2 lateral "wings" and a lower keel | 1 upper banner, 2 lateral "wings" and a lower keel |
| Banner length | Approximately 1.2 cm | Approximately 0.7 cm | Approximately 0.9 cm |
| Banner width | Approximately 0.8 cm | Approximately 0.4 cm | Approximately 0.6 cm |
| Banner shape | Orbicular, when unfurled | Orbicular, when unfurled | Orbicular, when unfurled |
| Banner margin | Entire | Entire | Entire |
| Banner apex | Mucronate | Mucronate | Mucronate |
| Banner base | Obtuse | Obtuse | Obtuse |
| Banner texture | Smooth, glabrous all surfaces | Smooth, glabrous all surfaces | Smooth, glabrous all surfaces |
| Banner aspect | Folded, margins furled | Folded, margins furled | Folded, margins furled |
| Banner color when opening, outer surface | Near RHS White 155A large basal blotch near RHS Purple 77A | Base near RHS White N155C remaining surface near RHS Red-Purple 61C | Near RHS Yellow 7C |
| Banner color when opening, inner surface | Near RHS White 155A large basal blotch near RHS Purple 77B | Base near RHS White N155C remaining surface near RHS Greyed-Purple 186C | Near RHS Yellow 7C |
| Banner color when opened, outer surface | Near RHS White 155A large basal blotch near RHS Violet 86A | Base near RHS White 155D, remaining surface near RHS Red 53A | Near RHS Yellow 7C |
| Banner color when opened, inner surface | Near RHS White 155A large basal blotch near RHS Violet 86C | Base near RHS White N155D, remaining surface near RHS Red-Purple 64A | Near RHS Yellow 7C |
| Banner color when fading, outer surface | Near RHS White 155A large basal blotch near RHS Violet 86C | Base near RHS White N155D, remaining surface near RHS Red-Purple 70A and 70C | Near RHS Yellow 7C |

TABLE 2-continued

Botanical characteristics of dwarf varieties 'LMIBW03-0', 'LMIRE05-0', and 'LMIYE06-0'

| | 'LMIBW03-0' | 'LMIRE05-0' | 'LMIYE06-0' |
|---|---|---|---|
| Banner color when fading, inner surface | Near RHS White 155A large basal blotch near Violet 86D | Base near RHS White N155D, remaining surface Red-Purple 70A and 70C | Near RHS Yellow 7C |
| Wing length | Approximately 1.2 cm | Approximately 1.1 cm | Approximately 0.9 cm |
| Wing width | Approximately 0.9 cm | Approximately 0.7 cm | Approximately 0.6 cm |
| Wing shape | Ovate | Ovate | Kidney shaped |
| Wing margin | Entire | Entire | Entire |
| Wing apex | Rounded, frequently fused to opposite wing at apex | Rounded, frequently fused to opposite wing at apex | Rounded, frequently fused to opposite wing at apex |
| Wing base | Truncate | Truncate | Truncate |
| Wing texture | Smooth, glabrous all surfaces | Smooth, glabrous all surfaces | Smooth, glabrous all surfaces |
| Wing aspect | Inwardly cupped | Inwardly cupped | Inwardly cupped |
| Wing color when opening, outer surface | Near RHS Purple-Violet N81A, lower section RHS N81B, base flushed with RHS White 155A | Near RHS Red 53C | Near RHS Yellow 4D |
| Wing color when opening, inner surface | Near RHS Violet 84A, lower section RHS N82D, base very slightly flushed with RHS White 155A | Near RHS Red 53C | Near RHS Yellow 4D |
| Wing color when opened, outer surface | Near RHS Purple-Violet N82A, very small section of base near RHS Violet 84D | Near RHS Red 53D | Near RHS Yellow 4C |
| Wing color when opened, inner surface | Near RHS Violet 86A, base near RHS Violet 84D | Near RHS Red 53D | Near RHS Yellow 4C |
| Wing color when fading, outer surface | Near RHS Violet-Blue 86A, flushed RHS Violet 83C, small section of base RHS Violet 84C | Near RHS Red 52A | Near RHS Yellow 4C |
| Wing color when fading, inner surface | Near RHS Violet 86B, streaks of RHS 84C and 84D emerging from base | Near RHS Red 52A | Near RHS Yellow 4C |
| Keel length | Approximately 1.1 cm | Approximately 0.7 cm | Approximately 0.7 cm |
| Keel width | Approximately 0.4 cm | Approximately 0.3 cm | Approximately 0.3 cm |
| Keel shape | Scythe | Scythe | Scythe |
| Keel margin | Entire | Entire | Entire |
| Keel apex | Awn-like | Awn-like | Awn-like |
| Keel base | Truncate | Truncate | Truncate |
| Keel texture | Smooth, glabrous all surfaces | Smooth, glabrous all surfaces | Smooth, glabrous all surfaces |
| Keel aspect | Folded | Folded | Folded |
| Keel color when opening, outer surface | Near RHS White 155A, apex RHS Violet 86A | Near RHS Red 52A | Near RHS Yellow-Green 150D |
| Keel color when opening, inner surface | Near RHS White 155A, apex RHS Violet 86A | Near RHS Red 52A | Near RHS Yellow-Green 150D |
| Keel color when opened, outer surface | Near RHS Violet 84D, apex RHS Violet 86A | Near RHS Red 52B | Near RHS Yellow 4D |
| Keel color when opened, inner surface | Near RHS Violet 84D, apex Violet 86A | Near RHS Red 52A | Near RHS Yellow 4D |
| Keel color when fading, outer surface | Near RHS Violet 84D, apex RHS Violet 86A | Near RHS Red 52C | Near RHS Yellow 4D |
| Keel color when fading, inner surface | Near RHS Violet 84D, apex RHS Violet 86A | Near RHS Red 52C | Near RHS Yellow 4D |
| Bud shape | Flattened ovate | Flattened ovate | Flattened, kidney shaped |

TABLE 2-continued

Botanical characteristics of dwarf varieties 'LMIBW03-0', 'LMIRE05-0', and 'LMIYE06-0'

| | 'LMIBW03-0' | 'LMIRE05-0' | 'LMIYE06-0' |
|---|---|---|---|
| Bud length | Approximately 1.1 cm | Approximately 1.5 cm | Approximately 0.8 cm |
| Bud diameter | Approximately 0.7 cm | Approximately 1.0 cm | Approximately 0.6 cm |
| Bud color | Lower side near RHS Purple-Violet N82A, upperside near RHS Green-White 157A | Lower side near RHS Red 52A blushed RHS 53A, upper side near RHS Red-Purple N57C | Near RHS Green-White 157A, flushed and striped RHS Green-Yellow 1D |
| Sepal quantity | 2, one fully developed, one minute (less than 1 mm in length), sometimes missing | 2, one fully developed, one minute (less than 1 mm in length), sometimes missing | 2, one fully developed, one minute (less than 1 mm in length), sometimes missing |
| Sepal length | Approximately 3 mm | Approximately 3 mm | Approximately 3 mm |
| Sepal width | Approximately 2 mm | Approximately 2 mm | Approximately 2 mm |
| Sepal shape | Deltate | Deltate | Deltate |
| Sepal aspect | Cupped | Cupped | Cupped |
| Sepal apex | Mucronate | Mucronate | Mucronate |
| Sepal margin | Entire | Entire | Entire |
| Sepal color, inner surface | RHS Yellow-Green 145C | RHS Yellow-Green 145C | RHS Yellow-Green 145D |
| Sepal color, outer surface | RHS Yellow-Green 145D | RHS Yellow-Green 145D | RHS Yellow-Green 145D |
| Sepal texture | Glabrous | Glabrous | Glabrous |
| Fragrance | Moderate | Strong, sweet scent | Moderate |
| Stamen quantity | Approximately 5 to 10 | Approximately 5 to 10 | Approximately 5 to 10 |
| Filament length | Approximately 0.4 cm | Approximately 0.4 cm | Approximately 0.4 cm |
| Filament color | Near RHS Yellow-Green 145D | Near RHS Yellow-Green 145D | Near RHS Yellow-Green 145D |
| Anther length | 0.2 cm | 0.1 cm | 0.1 cm |
| Anther shape | Elongated ovoid | Elongated ovoid | Elongated ovoid |
| Anther color | Near RHS Yellow-Green 145B | Near RHS Yellow-Orange 15B | Near RHS Yellow 9A |
| Pollen | Scant, colored near Yellow RHS 13A | Scant or absent, colored near Yellow RHS 13C | Scant or absent, colored near Yellow RHS 9C |
| Pistil quantity | 1 | 1 | 1 |
| Pistil length | Approximately 0.8 cm | Approximately 0.7 cm | Approximately 0.7 cm |
| Stigma shape | Globular | Globular | Globular |
| Stigma color | Near RHS Yellow-Green 145C | Near RHS Yellow-Orange 15B | Near RHS Yellow-Green 145C |
| Ovary | Near RHS Yellow-Green 145B, approximately 2 mm in diameter | Near RHS Green 143D, approximately 2 mm in diameter | Near RHS Yellow-Green 145C, approximately 2 mm in diameter |

Table 3 below lists some of the additional botanical characteristics of 'LMIBY04-0', also known as KELPIE 'Blue Yellow', and 'LMIRW01-0', also known as KELPIE 'Rose White' and 'Dupline Red'. These dwarf lines all exhibit the year round flowering characteristic, meaning they will flower absent of any cold treatment or vernalization, and/or regardless of day length, and are tolerant to USDA zones 3 to 9. They are compact, herbaceous vigorous perennials with a mounding foliar base topped with upright raceme inflorescences. The plant height to the top of the flowering plane for these dwarf lines does not exceed 35.0 cm. The leaves emerge directly from the base of the plant, or infrequently occur directly on the flowering stem. The leaves are orbicular shaped and palmately compound, occurring mainly as basal whorls, or infrequently alternate along the flowering stem. The inflorescence consists of single, large, papilonaceous flowers evenly and symmetrically arranged on racemes, with individual flowers lasting approximately 15 days.

TABLE 3

Botanical characteristics of dwarf varieties 'LMIBY04-0' and 'LMIRW01-0'

| | 'LMIBY04-0' | 'LMIRW01-0' |
|---|---|---|
| Spread | Approximately 20 cm | Approximately 15 to 22 cm |
| Leaf length | Range 5.0 cm to 8.0 cm | 9.0 cm |
| Leaf diameter | Range 5.0 cm to 7.5 cm | 8.5 cm |

TABLE 3-continued

Botanical characteristics of dwarf varieties 'LMIBY04-0' and 'LMIRW01-0'

| | 'LMIBY04-0' | 'LMIRW01-0' |
|---|---|---|
| Leaf quantity | Approximately 25 basal leaves, per plant. Average range 2 to 4 floral stem leaves, per stem | Approximately 20 to 30 basal leaves, per plant. Average range 4 to 8 floral stem leaves |
| Leaflets quantity | Average 11 | Range 9 to 12 |
| Leaflets shape | Oblanceolate | Oblanceolate |
| Leaflets arrangement | Radial | Radial |
| Leaflets length | Longest leaflet per leaf average 3.0 cm to 4.0 cm; Shortest leaflet per leaf average 2.4 cm to 3.0 cm | Longest leaflet per leaf average 4.8 cm; Shortest leaflet per leaf average 2.7 cm |
| Leaflets width | Central leaflet average 1.9 cm | Central leaflet average 1.6 cm |
| Leaflets apex | Acute to nearly acuminate | Acute to nearly acuminate |
| Leaflets base | Attenuate | Attenuate |
| Leaflets margin | Entire | Entire |
| Leaflets texture, both surfaces | Glabrous | Glabrous |
| Leaflets appearance, both surfaces | Matte | Matte |
| Leaflets aspect | Flat to very slightly reflexed upward | Flat to very slightly reflexed downward |
| Leaflets color, upper surface | Near RHS Green 143A | Near RHS Green 139B |
| Leaflets color, lower surface | Near RHS Green 143B | Near RHS Green 139C |
| Venation type | Pinnate | Pinnate |
| Venation color, upper surface | Near RHS Yellow-Green 144C | Near RHS Yellow-Green 145A |
| Venation color, lower surface | Near RHS Green 141D | Near RHS Yellow-Green 145C |
| Petiole length | Range 7.0 cm to 11.0 cm | Range 5.0 cm to 9.0 cm |
| Petiole diameter | 0.3 cm to 0.4 cm | 0.3 cm |
| Petiole color | Near RHS Yellow-Green 144C; Often heavily flushed RHS Greyed-Purple 186A, or entirely colored RHS 186B. | Near RHS Yellow-Green 144D |
| Petiole texture | Very minutely hirsute | Minutely hirsute |
| Quantity of flowers | 40 to 70 flowers and buds per inflorescence. Typically 1 to 3 inflorescences per plant at one time | 40 to 80 flowers and buds per inflorescence. Typically 3 to 6 inflorescences per plant at one time |
| Inflorescence diameter | Approximately 4.5 cm | Approximately 4.5 cm |
| Inflorescence height | Range 10 cm to 20 cm | Range 10 cm to 18 cm |
| Flower length (excluding pedicel) | Approximately 1.5 cm | Approximately 1.1 cm |
| Flower height (excluding pedicel) | Average 0.9 cm | Average 1.0 cm |
| Peduncle length | Approximately 3.0 cm from uppermost leaf to lowermost flower | Approximately 4.0 cm from uppermost leaf to lowermost flower |
| Peduncle diameter | Approximately 1.0 cm | Approximately 0.7 cm |
| Peduncle color | Near RHS Yellow-Green 144C | Near RHS Yellow-Green 145A |
| Peduncle strength | Flexible, very strong | Flexible, moderately strong |
| Peduncle texture | Slight pubescence | Short pubescence |
| Pedicel length | Approximately 0.6 cm | Approximately 1.0 cm |
| Pedicel diameter | Approximately 0.2 cm | Approximately 0.1 cm |
| Pedicel color | Near RHS Greyed-Purple 186B | Near RHS Green 138D, very lightly flushed RHS Purple N77C at base |
| Pedicel strength | Strong | Strong |
| Pedicel texture | Slightly pubescent | Softly pubescent |
| Petal quantity and arrangement | 1 upper banner, 2 lateral "wings" and a lower keel | 1 upper banner, 2 lateral "wings" and a lower keel |
| Banner length | Approximately 1.0 cm | Approximately 1.0 cm |
| Banner width | Approximately 0.8 cm | Approximately 0.7 cm |
| Banner shape | Orbicular, when unfurled | Orbicular, when unfurled |
| Banner margin | Entire | Entire |
| Banner apex | Mucronate | Mucronate |
| Banner base | Obtuse | Obtuse |
| Banner texture | Smooth, glabrous all surfaces | Smooth, glabrous all surfaces |
| Banner aspect | Folded, margins furled | Folded, margins furled |
| Banner color when opening, outer surface | Near RHS Green-White 157D, flushed RHS Yellow 2D, large basal blotch near RHS Violet-Purple N82A | Upper section near RHS Green-White 157D, mid-section RHS Red-Purple 65D, basal blotch near RHS Red-Purple 71C |

TABLE 3-continued

Botanical characteristics of dwarf varieties 'LMIBY04-0' and 'LMIRW01-0'

| | 'LMIBY04-0' | 'LMIRW01-0' |
|---|---|---|
| Banner color when opening, inner surface | Near RHS Green-White 157D large basal blotch near RHS Violet-Purple N82A | Upper section near RHS Green-White 157D, mid-section RHS Red-Purple 65D, basal blotch near RHS Red-Purple 71C |
| Banner color when opened, outer surface | Apical section near RHS Yellow 5C, mid-section near RHS White 155D large basal blotch near RHS Violet-Purple N82A | Near RHS White N155D, base blotched RHS Red-Purple N66B |
| Banner color when opened, inner surface | Apical section near RHS Yellow 5D, mid-section near RHS White 155D large basal blotch near RHS Violet-Purple N82A | Near RHS White N155D, base blotched Red-Purple N66C |
| Banner color when fading, outer surface | Apex near RHS Yellow 5D. Apical section near RHS Yellow 2D, mid-section near RHS White 155D large basal blotch near RHS Violet N87B | Near RHS White N155D, base blotched RHS Red-Purple N66C |
| Banner color when fading, inner surface | Apex near RHS Yellow 5D. Apical section near RHS Yellow 2D, mid-section near RHS White 155D large basal blotch near RHS Violet N87C | Near RHS White N155D, base blotched RHS Red-Purple N66D |
| Wing length | Approximately 0.9 cm | Approximately 0.9 cm |
| Wing width | Approximately 0.5 cm | Approximately 0.7 cm |
| Wing shape | Ovate | Ovate |
| Wing margin | Entire | Entire |
| Wing apex | Rounded, frequently fused to opposite wing at apex | Rounded, frequently fused to opposite wing at apex |
| Wing base | Truncate | Truncate |
| Wing texture | Smooth, glabrous all surfaces | Smooth, glabrous all surfaces |
| Wing aspect | Inwardly cupped | Inwardly cupped |
| Wing color when opening, outer surface | Near RHS Purple-Violet N82A, lower section slightly flushed RHS Purple N79B, base slightly flushed with RHS White 155A | Near RHS Red-Purple N57C |
| Wing color when opening, inner surface | Near RHS Purple-Violet N82A, lower section slightly flushed RHS Purple N79B, base slightly flushed with RHS White 155A | Near RHS Red-Purple 65A |
| Wing color when opened, outer surface | Near RHS Purple-Violet N82A, small section of base near RHS Purple N79C. A few small streaks near RHS Yellow 2D | Near RHS Red-Purple 67B |
| Wing color when opened, inner surface | Near RHS Purple-Violet N82A, small section of base near RHS Purple N79C. A few small streaks near RHS Yellow 2D | Near RHS Red-Purple 67C |
| Wing color when fading, outer surface | Near RHS Purple-Violet N82B, small section of base near RHS Purple N79C. A few small streaks near RHS White 155A | Near RHS Red-Purple 73A, streaked RHS N74B |
| Wing color when fading, inner surface | Near RHS Purple-Violet N82B, small section of base near RHS Purple N79C. A few small streaks near RHS White 155A | Near RHS Red-Purple N74B |
| Keel length | Approximately 0.7 cm | Approximately 0.7 cm |
| Keel width | Approximately 0.4 cm | Approximately 0.4 cm |
| Keel shape | Scythe | Scythe |
| Keel margin | Entire | Entire |
| Keel apex | Awn-like | Awn-like |
| Keel base | Truncate | Truncate |
| Keel texture | Smooth, glabrous all surfaces | Smooth, glabrous all surfaces |
| Keel aspect | Folded | Folded |
| Keel color when opening, outer surface | Near RHS Yellow 2D, apex RHS Violet N81B | Near RHS Yellow-Green 150D, apex RHS Red-Purple 64B |
| Keel color when opening, inner surface | Near RHS Yellow 2D, apex RHS Violet N81B | Near RHS Yellow-Green 150D, apex RHS Red-Purple 64B |
| Keel color when opened, outer surface | Near RHS Yellow 4D, apex RHS Violet N82A | Near RHS White 155D, apex RHS Red-Purple 64C, very tip of apex RHS Red-Purple 64B |
| Keel color when opened, inner surface | Near RHS Yellow 4D, apex RHS Violet N82A | Near RHS Red-Purple 65D, apex RHS Red-Purple 64D, very tip of apex RHS Red-Purple 64B |

TABLE 3-continued

Botanical characteristics of dwarf varieties 'LMIBY04-0' and 'LMIRW01-0'

| | 'LMIBY04-0' | 'LMIRW01-0' |
|---|---|---|
| Keel color when fading, outer surface | Near RHS Yellow 2D, apex RHS Violet 84A | Near RHS Purple 75D, apex RHS Purple 77A, very tip of apex Purple N77A |
| Keel color when fading, inner surface | Near RHS Yellow 2D, apex RHS Violet 84A | Near RHS Purple 75D, apex RHS Purple 77A, very tip of apex Purple N77A |
| Bud shape | Flattened ovate | Flattened ovate |
| Bud length | Approximately 0.9 cm | Approximately 0.9 cm |
| Bud diameter | Approximately 0.6 cm | Approximately 0.5 cm |
| Bud color | Lower side near RHS Violet N82B, upperside near RHS Green-White 157A | Near RHS Green-White 157A, flushed RHS Red-Purple 63B |
| Sepal quantity | 2, one fully developed, one minute (less than 1 mm in length), sometimes missing | 2, one fully developed, one minute (less than 1 mm in length), sometimes missing |
| Sepal length | Approximately 3 mm | Approximately 3 mm |
| Sepal width | Approximately 2 mm | Approximately 2 mm |
| Sepal shape | Deltate | Deltate |
| Sepal aspect | Cupped | Cupped |
| Sepal apex | Mucronate | Mucronate |
| Sepal margin | Entire | Entire |
| Sepal color, inner surface | RHS Yellow-Green 145A, flushed RHS Greyed-Purple 186B | RHS Yellow-Green 144D |
| Sepal color, outer surface | RHS Yellow-Green 145C, flushed RHS Greyed-Purple 186B | RHS Yellow-Green 144C |
| Sepal texture | Glabrous | Glabrous |
| Fragrance | Moderate | Strong, sweet scent |
| Stamen quantity | Approximately 5 to 10 | Approximately 5 to 10 |
| Filament length | Approximately 0.4 cm | Approximately 0.4 cm |
| Filament color | Near RHS Yellow-Green 145D | Near RHS Yellow-Green 150D |
| Anther length | 0.1 cm | 0.1 cm |
| Anther shape | Elongated ovoid | Elongated ovoid |
| Anther color | Near RHS Yellow-Green 145B | Near RHS Yellow-Orange 23A |
| Pollen | Scant or absent, colored near Yellow RHS 13A | Scant or absent, colored near Yellow-Orange 23A |
| Pistil quantity | 1 | 1 |
| Pistil length | Approximately 0.5 cm | Approximately 0.7 cm |
| Stigma shape | Globular | Globular |
| Stigma color | Near RHS Yellow-Green 145C | Near RHS Yellow-Orange 18B |
| Ovary | Near RHS Yellow-Green 145B, approximately 2 mm in diameter | Near RHS Green 141D, approximately 2 mm in diameter. |

Table 4 below lists some of the additional botanical characteristics of '16ST-9', also known as STAIRCASE 'Purple', '16ST-15', also known as STAIRCASE 'Lavender-Blue', and '16ST-10', also known as STAIRCASE 'Blue'. These tall lines all exhibit the year round flowering characteristic, meaning they will flower absent of any cold treatment or vernalization, and/or regardless of day length, and are tolerant to USDA zones 3 to 9. They are compact, herbaceous vigorous perennials with a mounding foliar base topped with upright raceme inflorescences. The leaves emerge directly from the base of the plant, or infrequently occur directly on the flowering stem. The leaves are orbicular shaped and palmately compound, occurring mainly as basal whorls, or infrequently alternate along the flowering stem. The inflorescence consists of single, large, papilonaceous flowers evenly and symmetrically arranged on racemes, with individual flowers lasting approximately 15 days.

TABLE 4

Botanical characteristics of tall varieties '16ST-9', '16ST-15', and '16ST-10'

| | '16ST-9' | '16ST-15' | '16ST-10' |
|---|---|---|---|
| Height | Approximately 21 cm to top of foliar plane, approximately 40 cm to top of flowering plane | Approximately 25 cm to top of foliar plane, approximately 60 cm to top of flowering plane | Approximately 22 cm to top of foliar plane, approximately 55 cm to top of flowering plane |
| Spread | Approximately 44 cm | Approximately 45 cm | Approximately 41 cm |
| Leaf length | 11.0 cm to 13.0 cm | 10 cm to 11.5 cm | 10 cm to 12 cm |
| Leaf diameter | 13.0 cm | 10 cm to 11.5 cm | 10 cm to 11.5 cm |
| Leaf quantity | Approximately 40 basal leaves, per plant. Average range | Approximately 60 basal leaves, per plant. Average range | Approximately 60 basal leaves, per plant. Average range |

TABLE 4-continued

Botanical characteristics of tall varieties '16ST-9', '16ST-15', and '16ST-10'

| | '16ST-9' | '16ST-15' | '16ST-10' |
|---|---|---|---|
| | 2 to 6 floral stem leaves, per stem | 6 to 10 floral stem leaves, per stem | 6 to 10 floral stem leaves, per stem |
| Leaflets quantity | Average range is 9 to 11 | Average 11 | Average 10 to 12 |
| Leaflets shape | Oblanceolate | Oblanceolate | Oblanceolate |
| Leaflets arrangement | Radial | Radial | Radial |
| Leaflets length | Longest leaflet per leaf range 6.5 cm to 8.0 cm; Shortest leaflet per leaf average 4.5 cm | Longest leaflet per leaf range 6.0 cm to 6.8 cm; Shortest leaflet per leaf range 4.0 cm to 4.5 cm | Longest leaflet per leaf range 6.0 cm to 7.0 cm; Shortest leaflet per leaf range 4.0 cm to 5.0 cm |
| Leaflets width | Central leaflet average 1.4 cm | Central leaflet average 1.6 cm | Central leaflet average 1.6 cm |
| Leaflets apex | Acute to nearly acuminate | Acute to nearly acuminate | Acute to nearly acuminate |
| Leaflets base | Attenuate | Attenuate | Attenuate |
| Leaflets margin | Entire | Entire | Entire |
| Leaflets texture, both surfaces | Glabrous | Glabrous | Glabrous |
| Leaflets appearance, both surfaces | Matte | Matte | Matte |
| Leaflets aspect | Flat to very slightly reflexed upward | Flat to very slightly reflexed downward | Flat to very slightly reflexed upward |
| Leaflets color, upper surface | Near RHS Green 137B | Near RHS Green 137A | Near RHS Green 137A |
| Leaflets color, lower surface | Near RHS Green 138A | Near RHS Green N138C | Near RHS Green 138B |
| Venation type | Pinnate | Pinnate | Pinnate |
| Venation color, upper surface | Near RHS Yellow-Green 145C | Near RHS Yellow-Green 144C | Near RHS Yellow-Green 144C |
| Venation color, lower surface | Near RHS Yellow-Green 145B | Near RHS Green 138B | Near RHS Green 138B |
| Petiole length | Range 9.0 cm to 14.0 cm | Range 8.0 cm to 15.0 cm | Range 12.0 cm to 15.0 cm |
| Petiole diameter | 0.3 cm to 0.4 cm | 0.3 cm to 0.4 cm | 0.3 cm to 0.4 cm |
| Petiole color | Near RHS Yellow-Green 145C. Immature petioles flushed with RHS Greyed-Purple 187B along uppermost one third | Near RHS Yellow-Green 144D | Near RHS Yellow-Green 144B |
| Petiole texture | Minutely hirsute | Very minutely hirsute | Very minutely hirsute |
| Quantity of flowers | 50 to 120 flowers and buds per inflorescence. Typically 6 to 9 inflorescences per plant at one time | 80 to 140 flowers and buds per inflorescence. Typically 2 to 6 inflorescences per plant at one time | 80 to 110 flowers and buds per inflorescence. Typically 2 to 6 inflorescences per plant at one time |
| Inflorescence diameter | Approximately 6.5 cm to 7.5 cm | Approximately 6.5 cm | Approximately 8.0 cm |
| Inflorescence height | Range 18 cm to 28 cm | Range 25 cm to 45 cm | Range 25 cm to 40 cm |
| Flower length (excluding pedicel) | Approximately 2.0 cm | Approximately 2.2 cm | Approximately 2.1 cm |
| Flower height (excluding pedicel) | Average 1.7 cm | Average 2.0 cm | Average 1.5 cm |
| Peduncle length | Approximately 4.0 cm from uppermost leaf to lowermost flower | Approximately 18.0 cm from uppermost leaf to lowermost flower | Approximately 10.0 cm from uppermost leaf to lowermost flower |
| Peduncle diameter | Approximately 0.7 cm to 1.2 cm | Approximately 1.0 cm | Approximately 1.1 cm |
| Peduncle color | Near RHS Yellow-Green 145B | Near RHS Yellow-Green 144B | Near RHS Yellow-Green 144B |
| Peduncle strength | Flexible, very strong | Flexible, very strong | Flexible, very strong |
| Peduncle texture | Slight pubescence | Slight pubescence | Slight pubescence |
| Pedicel length | Approximately 1.2 cm | Approximately 1.5 cm | Approximately 1.3 cm |
| Pedicel diameter | Approximately 0.2 cm | Approximately 0.2 cm | Approximately 0.2 cm |
| Pedicel color | Near RHS Yellow-Green 145B. Lower section flushed with RHS Greyed-Purple | Near RHS Yellow-Green 144D | Near RHS Yellow-Green 144D |

TABLE 4-continued

Botanical characteristics of tall varieties '16ST-9', '16ST-15', and '16ST-10'

| | '16ST-9' | '16ST-15' | '16ST-10' |
|---|---|---|---|
| | | | 187B |
| Pedicel strength | Strong | Strong | Strong |
| Pedicel texture | Slightly pubescent | Slightly pubescent | Slightly pubescent |
| Petal quantity and arrangement | 1 upper banner, 2 lateral "wings" and a lower keel | 1 upper banner, 2 lateral "wings" and a lower keel | 1 upper banner, 2 lateral "wings" and a lower keel |
| Banner length | Approximately 1.8 cm | Approximately 1.6 cm | Approximately 2.0 cm |
| Banner width | Approximately 0.8 cm | Approximately 0.6 cm | Approximately 1.6 cm |
| Banner shape | Orbicular, when unfurled | Orbicular, when unfurled | Orbicular, when unfurled |
| Banner margin | Entire | Entire | Entire |
| Banner apex | Mucronate | Mucronate | Mucronate |
| Banner base | Obtuse | Obtuse | Obtuse |
| Banner texture | Smooth, glabrous all surfaces | Smooth, glabrous all surfaces | Smooth, glabrous all surfaces |
| Banner aspect | Folded, margins furled | Folded, margins furled | Folded, margins furled |
| Banner color when opening, outer surface | Near RHS Purple N79A, light streaking near RHS Purple-Violet N80A. Base near RHS N79B | Near RHS Purple 79D. Base near RHS Yellow-Green 145D | Near RHS Purple-Violet N82A, streaked RHS N82D. Basal blotch near RHS Green-White 157D |
| Banner color when opening, inner surface | Near RHS Purple 79D, margins RHS N79A | Near RHS Purple-Violet N82A. Basal blotch near RHS White 155D | Near RHS Purple-Violet N82B. Inner halo near RHS Greyed-Purple 187B. Basal blotch near RHS Green-White 157D |
| Banner color when opened, outer surface | Near RHS Purple N79C. Faint central streak RHS 79D | Near RHS Purple-Violet N82A. Central blotch near RHS Violet 84D | Near RHS Violet 83A, streaked RHS Purple-Violet N82D. Central blotch near RHS Green 130D |
| Banner color when opened, inner surface | Near RHS Purple 79B. Base near RHS Violet 84D. | Near RHS Violet 83A. Central blotch near RHS Violet 84D, flushed N82D | Near RHS Violet 86A, lightly streaked RHS Violet 85A. Central blotch near RHS White 155D |
| Wing length | Approximately 1.5 cm | Approximately 1.5 cm | Approximately 1.3 cm |
| Wing width | Approximately 1.0 cm | Approximately 1.0 cm | Approximately 1.1 cm |
| Wing shape | Kidney shaped | Kidney shaped | Kidney shaped |
| Wing margin | Entire | Entire | Entire |
| Wing apex | Rounded, frequently fused to opposite wing at apex | Rounded, frequently fused to opposite wing at apex | Rounded, frequently fused to opposite wing at apex |
| Wing base | Truncate | Truncate | Truncate |
| Wing texture | Smooth, glabrous all surfaces | Smooth, glabrous all surfaces | Smooth, glabrous all surfaces |
| Wing aspect | Inwardly cupped | Inwardly cupped | Inwardly cupped |
| Wing color when opening, outer surface | Near RHS Purple N79A, light streaking near RHS Purple-Violet N80A. Base near RHS N79B | Near RHS White 155D, large blotch near apex flushed RHS N82C | Near RHS White 155A, faintly flushed RHS 86A |
| Wing color when opening, inner surface | Near RHS Purple 79D, margins RHS N79A | Near RHS White 155D | Near RHS White 155A |
| Wing color when opened, outer surface | Near RHS Purple N79C. Faint central streak RHS 79D | Background color near RHS Violet N87D, flushed and heavily veined with RHS Violet 86A | Near RHS Violet 83B, flushed and veined with RHS Purple-Violet 80B. Basal blotch near RHS Violet 85B |
| Wing color when opened, inner surface | Near RHS Purple 79B. Base near RHS Violet 84D | Near RHS Violet 85A, veins near RHS Violet-Blue N89D | Near RHS Violet 83B, central section RHS Purple-Violet N82C, veins RHS 83B. Basal blotch near RHS Violet 85C |

TABLE 4-continued

Botanical characteristics of tall varieties '16ST-9', '16ST-15', and '16ST-10'

| | '16ST-9' | '16ST-15' | '16ST-10' |
|---|---|---|---|
| Keel length | Approximately 1.4 cm | Approximately 1.4 cm | Approximately 1.7 cm |
| Keel width | Approximately 0.65 cm | Approximately 0.5 cm | Approximately 0.7 cm |
| Keel shape | Scythe | Scythe | Scythe |
| Keel margin | Entire | Entire | Entire |
| Keel apex | Awn-like | Awn-like | Awn-like |
| Keel base | Truncate | Truncate | Truncate |
| Keel texture | Smooth, glabrous all surfaces | Smooth, glabrous all surfaces | Smooth, glabrous all surfaces |
| Keel aspect | Folded | Folded | Folded |
| Keel color when opening, outer surface | Near RHS Violet 84D, central margin flushed RHS Purple-Violet N81C. Apex near RHS Purple 79A | Near RHS Yellow-Green 150D. Apex near RHS Violet-Blue N89A | Near RHS Yellow-Green 145D. Apex near RHS Violet-Blue N89A |
| Keel color when opening, inner surface | Near RHS Violet 84D, central margin flushed RHS Purple-Violet N81C. Apex near RHS Purple 79A | Near RHS Yellow-Green 150D. Apex near RHS Violet-Blue N89A | Near RHS Yellow-Green 145D. Apex near RHS Violet-Blue N89A |
| Keel color when opened, outer surface | Near RHS Violet 84D, central margin flushed RHS Purple-Violet N81C. Apex near RHS Purple 79A | Near RHS White 155D, upper 2/3 flushed and veined RHS Violet-Blue 90B. Apex near RHS Violet-Blue N92A | Near RHS White N155B. Apex near RHS Violet-Blue N89A |
| Keel color when opened, inner surface | Near RHS Violet 84D, central margin flushed RHS Purple-Violet N81C. Apex near RHS Purple 79A | Near RHS White 155D, upper 2/3 flushed and veined RHS Violet-Blue 90B. Apex near RHS Violet-Blue N92A | Near RHS White N155B. Apex near RHS Violet-Blue N89A |
| Bud shape | Flattened, kidney shaped | Flattened, kidney shaped | Flattened, kidney shaped |
| Bud length | Approximately 1.4 cm | Approximately 1.6 cm | Approximately 1.5 cm |
| Bud diameter | Approximately 0.7 cm | Approximately 0.9 cm | Approximately 0.7 cm |
| Bud color | Near RHS Purple N77C. Base near RHS Green 141D | Near RHS Green-White 157A, upper section flushed RHS Violet 84A | Near RHS Yellow-Green 145C, upper section flushed RHS Purple-Violet N81B |
| Sepal quantity | 2, one fully developed, one minute (less than 1 mm in length), sometimes missing | 2, one fully developed, one minute (less than 1 mm in length), sometimes missing | 2, one fully developed, one minute (less than 1 mm in length), sometimes missing |
| Sepal length | Approximately 5 mm | Approximately 6 mm | Approximately 7 mm |
| Sepal width | Approximately 3 mm | Approximately 4 mm | Approximately 4 mm |
| Sepal shape | Deltate | Deltate | Deltate |
| Sepal aspect | Cupped | Cupped | Cupped |
| Sepal apex | Mucronate | Mucronate | Mucronate |
| Sepal margin | Entire | Entire | Entire |
| Sepal color, both surfaces | RHS Yellow-Green 145D | RHS Yellow-Green 144C | RHS Yellow-Green 144D |
| Sepal texture | Glabrous | Glabrous | Glabrous |
| Fragrance | Faint | Strong, sweet scent | Strong, sweet scent |
| Stamen quantity | Approximately 5 | Approximately 5 | Approximately 5 to 10 |
| Filament length | Approximately 0.7 cm | Approximately 0.9 cm | Approximately 0.9 cm |
| Filament color | Near RHS Yellow-Green 150D | Near RHS Yellow-Green 149D | Near RHS Green-White 157D |
| Anther length | 0.2 cm | 0.1 cm | 0.1 cm |
| Anther shape | Elongated ovoid | Linear | Linear |
| Anther color | Near RHS Yellow-Orange 17B | Near RHS Orange 26A | Near RHS Orange 24A |
| Pollen | Scant, colored near Greyed-Orange N167A | Moderate, colored near Orange N125A | Moderate, colored near Greyed-Orange N163B |
| Pistil quantity | 1 | 1 | 1 |
| Pistil length | Approximately 1.8 cm | Approximately 1.9 cm | Approximately 1.9 cm |

TABLE 4-continued

Botanical characteristics of tall varieties '16ST-9', '16ST-15', and '16ST-10'

| | '16ST-9' | '16ST-15' | '16ST-10' |
|---|---|---|---|
| Stigma shape | Globular | Globular | Globular |
| Stigma color | Near RHS Yellow-Green 145D | Near RHS Yellow-Green 145B | Near RHS Yellow-Green 145C |
| Ovary | Near RHS Yellow-Green 150D, approximately 3 mm in diameter | Near RHS Yellow-Green 145B, approximately 4 mm in diameter | Near RHS Yellow-Green 145C, approximately 4 mm in diameter |

Table 5 below lists some of the additional botanical characteristics of '16ST-14', also known as STAIRCASE 'Blue Yellow', 'LSDOR04-0', also known as STAIRCASE 'Orange Yellow' (U.S. Patent Application No. 62/604,473) and 'LSDRW03-0', also known as STAIRCASE 'Rose White' (U.S. Patent Application No. 62/604,472). These tall lines all exhibit the year round flowering characteristic, meaning they will flower absent of any cold treatment or vernalization, and/or regardless of day length, and are tolerant to USDA zones 3 to 9. They are compact, herbaceous vigorous perennials with a mounding foliar base topped with upright raceme inflorescences. The leaves emerge directly from the base of the plant, or infrequently occur directly on the flowering stem. The leaves are orbicular shaped and palmately compound, occurring mainly as basal whorls, or infrequently alternate along the flowering stem. The inflorescence consists of single, large, papilonaceous flowers evenly and symmetrically arranged on racemes, with individual flowers lasting approximately 15 days.

TABLE 5

Botanical characteristics of tall varieties '16ST-14, 'LSDOR04-0, and 'LSDRW03-0'

| | 16ST-14 | 'LSDOR04-0' | 'LSDRW03-0' |
|---|---|---|---|
| Height | Approximately 25 cm to top of foliar plane, approximately 55 to 65 cm to top of flowering plane | Approximately 25 cm to top of foliar plane, approximately 60 cm to top of flowering plane | Approximately 20 cm to top of foliar plane, approximately 48 cm to top of flowering plane |
| Spread | Approximately 40 cm | Approximately 35 cm | Approximately 35 cm |
| Leaf length | 9.0 cm to 11.0 cm | 10 cm to 12.0 cm | 12 cm |
| Leaf diameter | 9.0 cm to 11.0 cm | 10 cm to 15.0 cm | 11.5 cm |
| Leaf quantity | Approximately 50 basal leaves per plant. Range of 6 to 8 floral stem leaves, per stem | Approximately 20 to 25 basal leaves per plant. Range of 4 to 8 floral stem leaves per stem | Approximately 20 to 30 basal leaves per plant. Range of 8 to 14 floral stem leaves per stem |
| Leaflets quantity | Average 10 | Average 11 | Average 9 to 12 |
| Leaflets shape | Oblanceolate | Oblanceolate | Oblanceolate |
| Leaflets arrangement | Radial | Radial | Radial |
| Leaflets length | Longest leaflet per leaf range 6.0 cm to 7.0 cm; Shortest leaflet per leaf range 4.0 cm to 5.0 cm | Longest leaflet per leaf range 6.0 cm to 8.0 cm; Shortest leaflet per leaf average 4.5 cm | Longest leaflet per leaf average 6.5 cm; Shortest leaflet per leaf average 4. 7 cm |
| Leaflets width | Central leaflet average 1.9 cm | Central leaflet range 1.9 cm to 2.3 cm | Central leaflet average 1.6 cm |
| Leaflets apex | Acute to nearly acuminate | Acuminate | Acute to nearly acuminate |
| Leaflets base | Attenuate | Attenuate | Attenuate |
| Leaflets margin | Entire | Entire | Entire |
| Leaflets texture, both surfaces | Glabrous | Glabrous | Glabrous |
| Leaflets appearance, both surfaces | Matte | Matte | Matte |
| Leaflets aspect | Flat to very slightly reflexed upward | Flat to very slightly reflexed downward | Flat to very slightly reflexed downward |
| Leaflets color, upper surface | Near RHS Green 141A | Near RHS Green 137A | Near RHS Green 137B |
| Leaflets color, lower surface | Near RHS Green 141C | Near RHS Green 138A | Near RHS Green 138A |
| Venation type | Pinnate | Pinnate | Pinnate |
| Venation color, upper surface | Near RHS Yellow-Green 144C | Near RHS Yellow-Green 145A | Near RHS Yellow-Green 145A |
| Venation color, lower surface | Near RHS Green 141D | Near RHS Yellow-Green 145B | Near RHS Green 145C |
| Petiole length | Range 12.0 cm to 15.0 cm | Range 6.0 cm to 16.0 cm | Range 8.0 cm to 11.0 cm |

TABLE 5-continued

Botanical characteristics of tall varieties '16ST-14, 'LSDOR04-0, and 'LSDRW03-0'

|  | 16ST-14 | 'LSDOR04-0' | 'LSDRW03-0' |
|---|---|---|---|
| Petiole diameter | 0.3 cm to 0.4 cm | 0.5 cm | 0.4 cm |
| Petiole color | Near RHS Yellow-Green 144C | Near RHS Yellow-Green 145B | Near RHS Yellow-Green 144D |
| Petiole texture | Very minutely hirsute | Minutely hirsute | Minutely hirsute |
| Quantity of flowers | 70 to 100 flowers and buds per inflorescence. Typically 2 to 6 inflorescences per plant at one time | 60 to 110 flowers and buds per inflorescence. Typically 4 to 6 inflorescences per plant at one time | 40 to 120 flowers and buds per inflorescence. Typically 4 to 5 inflorescences per plant at one time |
| Inflorescence diameter | Approximately 7.5 cm | Approximately 7.5 cm | Approximately 7.5 cm |
| Inflorescence height | Range 20 cm to 40 cm | Range 25 cm to 45 cm | Range 20 cm to 45 cm |
| Flower length (excluding pedicel) | Approximately 2.1 cm | Approximately 1.9 cm | Approximately 1.9 cm |
| Flower height (excluding pedicel) | Average range 1.8 cm | Average range 1.7 cm | Average range 2.0 cm |
| Peduncle length | Approximately 10.0 cm from uppermost leaf to lowermost flower | Approximately 7.0 cm from uppermost leaf to lowermost flower | Approximately 7.0 cm from uppermost leaf to lowermost flower |
| Peduncle diameter | Approximately 1.1 cm | Approximately 0.8 cm | Approximately 0.7 cm |
| Peduncle color | Near RHS Green 141C | Near RHS Yellow-Green N144D | Near RHS Yellow-Green 145A |
| Peduncle strength | Flexible, very strong | Flexible, very strong | Flexible, moderately strong |
| Peduncle texture | Slight pubescence | Short pubescence | Short pubescence |
| Pedicel length | Approximately 1.2 cm | Approximately 1.0 cm | Approximately 1.0 cm to 1.5 cm |
| Pedicel diameter | Approximately 0.2 cm | Approximately 0.2 cm | Approximately 0.15 cm |
| Pedicel color | Near RHS Grey ed-Red 180D | Near RHS Yellow-Green 145B | Near RHS Green 138D, flushed Purple N77C |
| Pedicel strength | Strong | Strong | Strong |
| Pedicel texture | Slightly pubescent | Softly pubescent | Softly pubescent |
| Petal quantity and arrangement | 1 upper banner, 2 lateral "wings" and a lower keel | 1 upper banner, 2 lateral "wings" and a lower keel | 1 upper banner, 2 lateral "wings" and a lower keel |
| Banner length | Approximately 2.0 cm | Approximately 1.7 cm | Approximately 2.0 cm |
| Banner width | Approximately 1.7 cm | Approximately 0.8 cm | Approximately 1.0 cm |
| Banner shape | Orbicular, when unfurled | Orbicular, when unfurled | Orbicular, when unfurled |
| Banner margin | Entire | Entire | Entire |
| Banner apex | Mucronate | Mucronate | Mucronate |
| Banner base | Obtuse | Obtuse | Obtuse |
| Banner texture | Smooth, glabrous all surfaces | Smooth, glabrous all surfaces | Smooth, glabrous all surfaces |
| Banner aspect | Folded, margins furled | Folded, margins furled | Folded, margins furled |
| Banner color when opening, outer surface | Near RHS Green-White 157D, flushed RHS Yellow 4C, large basal blotch near RHS Violet-Purple N82C | Near RHS Yellow 4A | Upper section near RHS Yellow-Green 150D, mid-section RHS Red-Purple 65D, basal blotch near RHS Red-Purple 71A |
| Banner color when opening, inner surface | Near RHS Green-White 157D large basal blotch near RHS Violet-Purple N82D | Near RHS Yellow 4C | Near RHS Red-Purple 65D, basal blotch near RHS Red-Purple 71A |
| Banner color when opened, outer surface | Apical section near RHS Yellow 7C, mid-section near RHS White 155D large basal blotch near RHS Violet 86A | Near RHS Yellow 8B, center stripe RHS7A | Near RHS White N155D, base blotched RHS Red-Purple 70A |
| Banner color when opened, inner surface | Apical section near RHS Yellow 7D, mid-section near | Near RHS Yellow 9D, center stripe RHS8A | Near RHS White N155D, base blotched RHS Red- |

TABLE 5-continued

Botanical characteristics of tall varieties '16ST-14, 'LSDOR04-0, and 'LSDRW03-0'

|  | 16ST-14 | 'LSDOR04-0' | 'LSDRW03-0' |
|---|---|---|---|
|  | RHS White 155D large basal blotch near RHS Violet 86D |  | Purple 70A |
| Banner color when fading, outer surface | Apex near Yellow 5C. Apical section near RHS Yellow 4D, mid-section near RHS White 155D large basal blotch near RHS Violet N88B | Near RHS Yellow 8B, center stripe RHS8A | Near RHS White N155D, base blotched RHS Red-Purple 70A and 70C |
| Banner color when fading, inner surface | Apex near Yellow 5C. Apical section near RHS Yellow 4D, mid-section near RHS White 155D large basal blotch near RHS Violet N88C | Near RHS Yellow 9D, center stripe RHS8A | Near RHS White N155D, base blotched RHS Red-Purple 70A and 70C |
| Wing length | Approximately 1.6 cm | Approximately 1.5 cm | Approximately 1.7 cm |
| Wing width | Approximately 0.9 cm | Approximately 1.0 cm | Approximately 1.0 cm |
| Wing shape | Ovate | Ovate | Ovate |
| Wing margin | Entire | Entire | Entire |
| Wing apex | Rounded, frequently fused to opposite wing at apex | Rounded, frequently fused to opposite wing at apex | Rounded, frequently fused to opposite wing at apex |
| Wing base | Truncate | Truncate | Truncate |
| Wing texture | Smooth, glabrous all surfaces | Smooth, glabrous all surfaces | Smooth, glabrous all surfaces |
| Wing aspect | Inwardly cupped | Inwardly cupped | Inwardly cupped |
| Wing color when opening, outer surface | Near RHS Purple-Violet N82B, lower section RHS N82A, base slightly flushed with RHS White 155A | Near RHS Yellow 12C, flushed RHS Orange-Red N34C | Near RHS Yellow-Green 150D |
| Wing color when opening, inner surface | Near RHS Purple-Violet N82B, lower section RHS N82A, base slightly flushed with RHS White 155A | Near RHS Yellow 12D, slightly flushed RHS Orange-Red N34C | Near RHS Red-Purple 65D |
| Wing color when opened, outer surface | Near RHS Violet-Blue 90C, small section of base near RHS Violet 83A. A few small streaks near RHS Yellow 5D | Near RHS Orange-Red 35A, stripes RHS yellow 12C | Near RHS Red-Purple 71D |
| Wing color when opened, inner surface | Near RHS Violet-Blue 90D, small section of base near RHS Violet 83A. Moderate small streaks near RHS Yellow 5D | Near RHS Yellow 13D, stripes RHS Orange-Red 35C | Near RHS Red-Purple 73A |
| Wing color when fading, outer surface | Near RHS Violet-Blue 94C, small section of base near 94B. Moderate small streaks near RHS White 155A | Near RHS Orange-Red 35B, stripes RHS yellow 12C | Near RHS Red-Purple 73A, streaked RHS N74B |
| Wing color when fading, inner surface | Near RHS Violet-Blue 94C, small section of base near RHS 94B. Moderate small streaks near RHS White 155A | Near RHS Yellow 13D, stripes RHS Orange-Red 3 5C | Near RHS Red-Purple N74B |
| Keel length | Approximately 1.3 cm | Approximately 1.2 cm | Approximately 1.4 cm |
| Keel width | Approximately 0.5 cm | Approximately 0.5 cm | Approximately 0.7 cm |
| Keel shape | Scythe | Scythe | Scythe |
| Keel margin | Entire | Entire | Entire |
| Keel apex | Awn-like | Awn-like | Awn-like |

TABLE 5-continued

Botanical characteristics of tall varieties '16ST-14, 'LSDOR04-0, and 'LSDRW03-0'

| | 16ST-14 | 'LSDOR04-0' | 'LSDRW03-0' |
|---|---|---|---|
| Keel base | Truncate | Truncate | Truncate |
| Keel texture | Smooth, glabrous all surfaces | Smooth, glabrous all surfaces | Smooth, glabrous all surfaces |
| Keel aspect | Folded | Folded | Folded |
| Keel color when opening, outer surface | Near RHS Yellow 4D, apex RHS Violet N88C | Near RHS Yellow 11D, apex RHS Greyed-Purple 187A | Near RHS Yellow-Green 150D, apex RHS Purple N79B |
| Keel color when opening, inner surface | Near RHS Yellow 4D, apex Violet N88C | Near RHS Yellow 11D, apex Greyed-Purple 187A | Near RHS Yellow-Green 150D, apex Purple N79C |
| Keel color when opened, outer surface | Near RHS Yellow 4C, apex RHS Violet-Blue 90B | Near RHS Yellow 4D, apex RHS Greyed-Purple 187A | Near RHS White 155D, apex RHS Purple 77A, very tip of apex RHS Purple N77A |
| Keel color when opened, inner surface | Near RHS Yellow 4C, apex RHS Violet-Blue 90C | Near RHS Yellow 4D, apex RHS Greyed-Purple 187A | Near RHS Purple 75D, apex RHS Purple 77A, very tip of apex RHS Purple N77A |
| Keel color when fading, outer surface | Near RHS Yellow 5D, apex RHS Violet-Blue 91A | Near RHS White 155D, RHS Greyed-Purple 187A | Near RHS Purple 75D, apex RHS Purple 77A, very tip of apex RHS Purple N77A |
| Keel color when fading, inner surface | Near RHS Yellow 5D, apex RHS Violet-Blue 91A | Near RHS White 155D, RHS Greyed-Purple 187A | Near RHS Purple 75D, apex RHS Purple 77A, very tip of apex RHS Purple N77A |
| Bud shape | Flattened ovate | Flattened ovate | Flattened ovate |
| Bud length | Approximately 1.3 cm | Approximately 1.1 cm | Approximately 1.5 cm |
| Bud diameter | Approximately 0.8 cm | Approximately 0.9 cm | Approximately 0.8 cm |
| Bud color | Lower side near RHS Violet N87B, upperside near RHS Green-White 157A | Near RHS Green-Yellow 1C | Near RHS Red-Purple 65D |
| Sepal quantity | 2, one fully developed, one minute (less than 1 mm in length), sometimes missing | 2, one fully developed, one minute (less than 1 mm in length), sometimes missing | 2, one fully developed, one minute (less than 1 mm in length), sometimes missing |
| Sepal length | Approximately 4 mm | Approximately 6 mm | Approximately 5 mm |
| Sepal width | Approximately 3 mm | Approximately 4 mm | Approximately 4 mm |
| Sepal shape | Deltate | Deltate | Deltate |
| Sepal aspect | Cupped | Cupped | Cupped |
| Sepal apex | Mucronate | Mucronate | Mucronate |
| Sepal margin | Entire | Entire | Entire |
| Sepal color, upper surface | RHS Yellow-Green 145A, flushed RHS Greyed-Purple 186B | RHS Yellow-Green 145C | RHS Yellow-Green 144D |
| Sepal color, lower surface | RHS Yellow-Green 145C, flushed RHS Greyed-Purple 186B | RHS Yellow-Green 145C | RHS Yellow-Green 144C |
| Sepal texture | Glabrous | Glabrous | Glabrous |
| Fragrance | Moderate scent | Strong, sweet scent | Strong, sweet scent |
| Stamen quantity | Approximately 5 to 10 | Approximately 8 | Approximately 8 |
| Filament length | Approximately 0.7 cm | Approximately 0.5 cm | Approximately 0.5 cm |
| Filament color | Near RHS Yellow-Green 145D | Near RHS Yellow-Green 145D | Near RHS Yellow-Green 150D |
| Anther length | 0.2 cm | 0.2 cm | 0.3 cm |
| Anther shape | Elongated ovoid | Elongated ovoid | Elongated ovoid |
| Anther color | Near RHS Yellow-Green 145B | Near RHS Yellow-Green 145B | Near RHS Yellow-Orange 23A |
| Pollen | Scant, colored near RHS Yellow-Orange 23A | Scant, colored near RHS Yellow-Orange 21A | Scant, colored near RHS Yellow-Orange 23A |
| Pistil quantity | 1 | 1 | 1 |
| Pistil length | Approximately 1.1 cm | Approximately 1.1 cm | Approximately 1.5 cm |

TABLE 5-continued

Botanical characteristics of tall varieties '16ST-14, 'LSDOR04-0, and 'LSDRW03-0'

| | 16ST-14 | 'LSDOR04-0' | 'LSDRW03-0' |
|---|---|---|---|
| Stigma shape | Globular | Globular | Globular |
| Stigma color | Near RHS Yellow-Green 145C | Near RHS Yellow-Green 145D | Near RHS Yellow-Orange 18B |
| Ovary | Near RHS Yellow-Green 145B, approximately 2 mm in diameter | Near RHS Yellow-Green 145C, approximately 2 mm in diameter | Near RHS Green 141D, approximately 2 mm in diameter |

Table 6 below lists some of the additional botanical characteristics of 'LSTRE04-0', also known as STAIRCASE 'Red' (U.S. Patent Application No. 62/604,475), 'LSTBL01-0', also known as STAIRCASE 'Sky Blue' (U.S. Patent Application No. 62/604,474), and 'LSTYE05-0', also known as STAIRCASE 'Yellow' (U.S. Patent Application No. 62/604,476). These tall lines all exhibit the year round flowering characteristic, meaning they will flower absent of any cold treatment or vernalization, and/or regardless of day length, and are tolerant to USDA zones 3 to 9. They are compact, herbaceous vigorous perennials with a mounding foliar base topped with upright raceme inflorescences. The leaves emerge directly from the base of the plant, or infrequently occur directly on the flowering stem. The leaves are orbicular shaped and palmately compound, occurring mainly as basal whorls, or infrequently alternate along the flowering stem. The inflorescence consists of single, large, papilonaceous flowers evenly and symmetrically arranged on racemes, with individual flowers lasting approximately 15 days.

TABLE 6

Botanical characteristics of tall varieties 'LSTRE04-0, 'LSTBL01-0', and 'LSTYE05-0'

| | 'LSTRE04-0' | 'LSTBL01-0' | 'LSTYE05-0' |
|---|---|---|---|
| Height | Approximately 25 cm to top of foliar plane, approximately 65 cm to top of flowering plane | Approximately 20 cm to top of foliar plane, approximately 50 cm to top of flowering plane | Approximately 28 cm to top of foliar plane, approximately 60 cm to top of flowering plane |
| Spread | Approximately 40 cm | Approximately 35 cm | Approximately 40 cm |
| Leaf length | 12.0 cm | 7.0 cm to 11.0 cm | 11.0 cm to 13.0 cm |
| Leaf diameter | 13.0 cm | 7.0 cm to 11.0 cm | 13.0 cm |
| Leaf quantity | Approximately 20 to 30 basal leaves, per plant. Range of 2 to 4 floral stem leaves, per stem | Approximately 20 to 30 basal leaves, per plant. Range of 6 to 12 floral stem leaves, per stem | Approximately 20 basal leaves, per plant. Range of 4 to 8 floral stem leaves, per stem |
| Leaflets quantity | Range 10 to 11 | Range 10 to 11 | Range 11 to 13 |
| Leaflets shape | Oblanceolate | Oblanceolate | Oblanceolate |
| Leaflets arrangement | Radial | Radial | Radial |
| Leaflets length | Longest leaflet per leaf average 7.5 cm; Shortest leaflet per leaf average 4.5 cm | Longest leaflet per leaf range 5.0 cm to 7.0 cm; Shortest leaflet per leaf average 4.5 cm | Longest leaflet per leaf range 7.0 cm to 10.0 cm; Shortest leaflet per leaf range 3.5 to 7.0 cm |
| Leaflets width | Central leaflet average 2.0 cm | Central leaflet range 1.6 cm to 2.0 cm | Central leaflet average 1.7 cm |
| Leaflets apex | Acute to nearly acuminate | Acute to nearly acuminate | Acute to nearly acuminate |
| Leaflets base | Attenuate | Attenuate | Attenuate |
| Leaflets margin | Entire | Entire | Entire |
| Leaflets texture, both surfaces | Glabrous | Glabrous | Glabrous |
| Leaflets appearance, both surfaces | Matte | Matte | Matte |
| Leaflets aspect | Flat to very slightly reflexed downward | Flat to very slightly reflexed downward | Flat to very slightly reflexed downward |
| Leaflets color, upper surface | Near RHS Green 137A | Near RHS Green 137B | Near RHS Green 141B |
| Leaflets color, lower surface | Near RHS Green 137D | Near RHS Green 138A | Near RHS Green 137D |
| Venation type | Pinnate | Pinnate | Pinnate |
| Venation color, upper surface | Near RHS Yellow-Green 145A | Near RHS Yellow-Green 145B | Near RHS Yellow-Green 145A |
| Venation color, lower surface | Near RHS Yellow-Green 145A | Near RHS Yellow-Green 144D | Near RHS Green 145C |
| Petiole length | Range 10.0 cm to 12.0 cm | Range 8.0 cm to 15.0 cm | Range 9.0 cm to 12.0 cm |

TABLE 6-continued

Botanical characteristics of tall varieties 'LSTRE04-0, 'LSTBL01-0', and 'LSTYE05-0'

| | 'LSTRE04-0' | 'LSTBL01-0' | 'LSTYE05-0' |
|---|---|---|---|
| Petiole diameter | 0.6 cm | 0.5 cm | 0.4 cm |
| Petiole color | Near RHS Yellow-Green 144D | Near RHS Yellow-Green 144C | Near RHS Yellow-Green 145C |
| Petiole texture | Minutely hirsute | Minutely hirsute | Minutely hirsute |
| Quantity of flowers | 60 to 130 flowers and buds per inflorescence. Typically 4 to 6 inflorescences per plant at one time | 40 to 100 flowers and buds per inflorescence. Typically 5 to 8 inflorescences per plant at one time | 40 to 160 flowers and buds per inflorescence. Typically 5 to 9 inflorescences per plant at one time |
| Inflorescence diameter | Approximately 8.0 cm | Approximately 8.0 cm | Approximately 9.0 cm to 12.0 cm |
| Inflorescence height | Range 20 cm to 45 cm | Range 15 cm to 30 cm | Range 19 cm to 45 cm |
| Flower length (excluding pedicel) | Approximately 1.9 cm | Approximately 2.2 cm | Approximately 2.5 cm |
| Flower height (excluding pedicel) | Average 2.0 cm | Average 1.8 cm | Average 2.1 cm |
| Peduncle length | Approximately 7.0 cm from uppermost leaf to lowermost flower | Approximately 5.0 cm from uppermost leaf to lowermost flower | Approximately 7.0 cm from uppermost leaf to lowermost flower |
| Peduncle diameter | Approximately 0.9 cm | Approximately 0.8 cm | Approximately 0.8 cm |
| Peduncle color | Near RHS Yellow-Green 145A, flushed Greyed-Purple 187B | Near RHS Yellow-Green 145A | Near RHS Yellow-Green 145B |
| Peduncle strength | Flexible, very strong | Flexible, very strong | Flexible, very strong |
| Peduncle texture | Short pubescence | Short pubescence | Slight pubescence |
| Pedicel length | Approximately 1.5 cm | Approximately 1.5 cm | Approximately 1.2 cm |
| Pedicel diameter | Approximately 0.2 cm | Approximately 0.2 cm | Approximately 0.2 cm |
| Pedicel color | Near RHS Greyed-Red 186B | Near RHS Yellow-Green 145A | Near RHS Yellow-Green 145B |
| Pedicel strength | Strong | Strong | Strong |
| Pedicel texture | Softly pubescent | Softly pubescent | Slightly pubescent |
| Petal quantity and arrangement | 1 upper banner, 2 lateral "wings" and a lower keel | 1 upper banner, 2 lateral "wings" and a lower keel | 1 upper banner, 2 lateral "wings" and a lower keel |
| Banner length | Approximately 2.0 cm | Approximately 1.7 cm | Approximately 1.8 cm |
| Banner width | Approximately 1.0 cm | Approximately 1.0 cm | Approximately 1.0 cm |
| Banner shape | Orbicular, when unfurled | Orbicular, when unfurled | Orbicular, when unfurled |
| Banner margin | Entire | Entire | Entire |
| Banner apex | Mucronate | Mucronate | Mucronate |
| Banner base | Obtuse | Obtuse | Obtuse |
| Banner texture | Smooth, glabrous all surfaces | Smooth, glabrous all surfaces | Smooth, glabrous all surfaces |
| Banner aspect | Folded, margins furled | Folded, margins furled | Folded, margins furled |
| Banner color when opening, outer surface | Base near RHS White N155C remaining surface near RHS Red-Purple 61C | Near RHS White 155A large basal blotch near RHS Purple 77A | Near RHS Yellow 7A |
| Banner color when opening, inner surface | Base near RHS White N155C remaining surface near RHS Greyed-Purple 186C | Near RHS White 155A large basal blotch near RHS Purple 79D | Near RHS Yellow 7A |
| Banner color when opened, outer surface | Base near RHS White 155D, remaining surface near RHS Red 53A | Near RHS White 155A large basal blotch near RHS Violet 86A | Near RHS Yellow 7A |
| Banner color when opened, inner surface | Base near RHS White N155D, remaining surface near RHS Red-Purple 64A | Near RHS White 155A large basal blotch near RHS Violet 86C | Near RHS Yellow 7A |

TABLE 6-continued

Botanical characteristics of tall varieties 'LSTRE04-0, 'LSTBL01-0', and 'LSTYE05-0'

|  | 'LSTRE04-0' | 'LSTBL01-0' | 'LSTYE05-0' |
| --- | --- | --- | --- |
| Banner color when fading, outer surface | Base near RHS White N155D, remaining surface near RHS Red-Purple 70A and 70C | Near RHS White 155A large basal blotch near RHS Violet 86C | Near RHS Yellow 7A |
| Banner color when fading, inner surface | Base near RHS White N155D, remaining surface RHS Red-Purple 70A and 70C | Near RHS White 155A large basal blotch near RHS Violet 86D | Near RHS Yellow 7A |
| Wing length | Approximately 1.7 cm | Approximately 1.6 cm | Approximately 1.6 cm |
| Wing width | Approximately 1.3 cm | Approximately 1.0 cm | Approximately 1.3 cm |
| Wing shape | Ovate | Ovate | Kidney shaped |
| Wing margin | Entire | Entire | Entire |
| Wing apex | Rounded, frequently fused to opposite wing at apex | Rounded, frequently fused to opposite wing at apex | Rounded, frequently fused to opposite wing at apex |
| Wing base | Truncate | Truncate | Truncate |
| Wing texture | Smooth, glabrous all surfaces | Smooth, glabrous all surfaces | Smooth, glabrous all surfaces |
| Wing aspect | Inwardly cupped | Inwardly cupped | Inwardly cupped |
| Wing color when opening, outer surface | Near RHS Red 53C | Near RHS Purple-Violet N81A, lower section RHS N81B, base flushed with RHS White 155A | Near RHS Yellow 7A |
| Wing color when opening, inner surface | Near RHS Red 53C | Near RHS Purple-Violet N82C, lower section N82D, base very slightly flushed with RHS White 155A | Near RHS Yellow 7A |
| Wing color when opened, outer surface | Near RHS Red 53D | Near RHS Violet 83A, very small section of base near RHS Violet 84D | Near RHS Yellow 7A |
| Wing color when opened, inner surface | Near RHS Red 53D | Near RHS Violet 86A, very small section of base near RHS Violet 84D | Near RHS Yellow 7A |
| Wing color when fading, outer surface | Near RHS Red 52A | Near RHS Violet-Blue N89A, flushed Violet 83B, small section of base RHS Violet 84C | Near RHS Yellow 7A |
| Wing color when fading, inner surface | Near RHS Red 52A | Near RHS Violet 86B, streaks of RHS 84C and 84D emerging from base | Near RHS Yellow 7A |
| Keel length | Approximately 1.2 cm | Approximately 1.4 cm | Approximately 1.4 cm |
| Keel width | Approximately 0.6 cm | Approximately 0.5 cm | Approximately 0.65 cm |
| Keel shape | Scythe | Scythe | Scythe |
| Keel margin | Entire | Entire | Entire |
| Keel apex | Awn-like | Awn-like | Awn-like |
| Keel base | Truncate | Truncate | Truncate |
| Keel texture | Smooth, glabrous all surfaces | Smooth, glabrous all surfaces | Smooth, glabrous all surfaces |
| Keel aspect | Folded | Folded | Folded |
| Keel color when opening, both surfaces | Near RHS Red 52A | Near RHS White 155A, apex RHS Violet 86A | Near RHS Yellow-Green 150D |
| Keel color when opened, outer surface | Near RHS Red 52B | Near RHS Violet 84D, apex RHS Violet 86A | Near RHS Yellow 4B |
| Keel color when opened, inner surface | Near RHS Red 52A | Near RHS Violet 84D, apex RHS Violet 86A | Near RHS Yellow 4B |
| Keel color when fading, both surfaces | Near RHS Red 52C | Near RHS Violet 84D, apex RHS Violet 86A | Near RHS Yellow 4B |
| Bud shape | Flattened ovate | Flattened ovate | Flattened kidney shaped |

TABLE 6-continued

Botanical characteristics of tall varieties 'LSTRE04-0, 'LSTBL01-0', and 'LSTYE05-0'

|  | 'LSTRE04-0' | 'LSTBL01-0' | 'LSTYE05-0' |
|---|---|---|---|
| Bud length | Approximately 1.5 cm | Approximately 1.5 cm | Approximately 1.5 cm |
| Bud diameter | Approximately 1.0 cm | Approximately 0.8 cm | Approximately 1.0 cm |
| Bud color | Lower side near RHS Red 52A blushed RHS 53A, upper side near RHS Red-Purple N57C | Lower side near RHS Purple-Violet N80B, upper side near RHS Green-White 157A | Near RHS Green-White 157A, flushed and striped RHS Green-Yellow 1B |
| Sepal quantity | 2, one fully developed, one minute (less than 1 mm in length), sometimes missing | 2, one fully developed, one minute (less than 1 mm in length), sometimes missing | 2, one fully developed, one minute (less than 1 mm in length), sometimes missing |
| Sepal length | Approximately 5 mm | Approximately 4 mm | Approximately 6 mm |
| Sepal width | Approximately 4 mm | Approximately 3 mm | Approximately 4 mm |
| Sepal shape | Deltate | Deltate | Deltate |
| Sepal aspect | Cupped | Cupped | Cupped |
| Sepal apex | Mucronate | Mucronate | Mucronate |
| Sepal margin | Entire | Entire | Entire |
| Sepal color, upper surface | RHS Yellow-Green 145C | RHS Yellow-Green 145C | RHS Yellow-Green 145C |
| Sepal color, lower surface | RHS Yellow-Green 145D | RHS Yellow-Green 145D | RHS Yellow-Green 145C |
| Sepal texture | Glabrous | Glabrous | Glabrous |
| Fragrance | Strong, sweet scent | Strong, sweet and spicy scent | Strong, sweet scent |
| Stamen quantity | Approximately 8 | Approximately 10 | Approximately 10 |
| Filament length | Approximately 0.9 cm | Approximately 0.6 cm | Approximately 0.6 cm |
| Filament color | Near RHS Yellow-Green 145D | Near RHS Yellow-Green 145D | Near RHS Yellow-Green 145D |
| Anther length | 0.3 cm | 0.2 cm | 0.2 cm |
| Anther shape | Elongated ovoid | Elongated ovoid | Elongated ovoid |
| Anther color | Near RHS Yellow-Orange 15B | Near RHS Yellow-Green 145B | Near RHS Greyed-Orange 168B |
| Pollen | Scant, colored near RHS Yellow 13C | Scant, colored near RHS Yellow-Orange 23A | Scant, colored near RHS Greyed-Orange N170A |
| Pistil quantity | 1 | 1 | 1 |
| Pistil length | Approximately 1.5 cm | Approximately 1.1 cm | Approximately 1.4 cm |
| Stigma shape | Globular | Globular | Globular |
| Stigma color | Near RHS Yellow-Orange 15B | Near RHS Yellow-Green 145C | Near RHS Yellow-Green 145C |
| Ovary | Near RHS Green 143D, approximately 2 mm in diameter | Near RHS Yellow-Green 145B, approximately 2 mm in diameter | Near RHS Green 145C, approximately 2 mm in diameter |

Further Embodiments

Characterization of the Year Round Flowering Lupine Recessive Allele Using Complementation Assays The recessive allele responsible for year round flowering of the lupine of the present application can be identified using complementation assays, which are well-known in the art. See for example, Griffiths et al. "An Introduction to Genetic Analysis" 7$^{th}$ Edition. W.H. Freeman (2000), explaining how a mutant condition that is determined by a recessive allele can be determined.

Breeding with Year Round Flowering Lupine

The goal of ornamental plant breeding is to develop new, unique and superior ornamental varieties and hybrids. The breeder initially selects and crosses two or more parental lines, followed by repeated selfing and selection, producing many new genetic combinations. The breeder can theoretically generate billions of different genetic combinations via crossing, selection, selfing and mutations. Therefore, a breeder will never develop the same variety genetically and having the same traits from the exact same parents.

Each year, the plant breeder selects the germplasm to advance to the next generation. This germplasm is grown under unique and different geographical, climatic and soil conditions and further selections are then made during and at the end of the growing season. The varieties that are developed are unpredictable because the breeder's selection occurs in unique environments with no control at the DNA level, and with millions of different possible genetic combinations being generated. A breeder of ordinary skill in the art cannot predict the final resulting lines he develops, except possibly in a very gross and general fashion. The same breeder cannot produce the same variety twice by using the same original parents and the same selection techniques. This unpredictability results in the expenditure of large amounts of research monies to develop superior new lupine varieties.

Breeding programs combine desirable traits from two or more varieties or various broad-based sources into breeding pools from which varieties are developed by selfing and selection of desired phenotypes. Pedigree breeding is used commonly for the improvement of self-pollinating plants. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Using Year Round Flowering Lupine to Develop Other Lupine Plants

Lupine, such as the year round flowering lupine are developed for sales in the ornamental and cut flower market. However, said lupine plants can also provide a source of breeding material that may be used to develop new lupine plants and varieties. Plant breeding techniques known in the art and used in a lupine plant breeding program include, but are not limited to, recurrent selection, mass selection, bulk selection, hybridization, mass selection, backcrossing, pedigree breeding, open-pollination breeding, restriction fragment length polymorphism enhanced selection, genetic marker enhanced selection, making double haploids, mutagenesis and transformation. Often combinations of these techniques are used. The development of lupine varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

Any plants produced using the lupine plants disclosed in the present application as at least one parent are also an embodiment. These methods are well-known in the art and some of the more commonly used breeding methods are described herein. Descriptions of breeding methods can be found in one of several reference books (e.g., Allard, "Principles of Plant Breeding" (1999); Vainstein, "Breeding for Ornamentals: Classical and Molecular Approaches," Kluwer Academic Publishers (2002); Callaway, "Breeding Ornamental Plants," Timber Press (2000); and Bragdø, Marie, "Inter-specific Crosses in *Lupinus*: Cytology and Inheritance of Flower Color," Institute of Genetics and Plant Breeding, Agricultural College of Norway, Vollebekk, Norway (Sep. 28, 1956).

Breeding steps that may be used in the lupine plant breeding program can include for example, pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

As used herein, the term "plant" includes plant cells, plant protoplasts, plant cell tissue cultures from which lupine plants can be regenerated, plant calli, plant clumps, and plant cells that are intact in plants or parts of plants, such as pollen, ovules, embryos, protoplasts, meristematic cells, callus, pollen, leaves, ovules, anthers, cotyledons, hypocotyl, pistils, roots, root tips, seeds, flowers, petiole, pods, shoot, or stems and the like.

Pedigree Breeding

Pedigree breeding starts with the crossing of two genotypes, such as year round flowering lupine and another different lupine having one or more desirable characteristics that is lacking or which complements the year round flowering lupine phenotype. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent and the desirable trait transferred from the donor parent.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a lupine plant may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new lupine varieties.

Therefore, another embodiment is a method of making a backcross conversion of year round flowering lupine, comprising the steps of crossing a plant of year round flowering lupine with a donor plant comprising a desired trait, selecting an $F_1$ progeny plant comprising the desired trait, and backcrossing the selected $F_1$ progeny plant to a plant of year round flowering lupine. This method may further comprise the step of obtaining a molecular marker profile of year round flowering lupine and using the molecular marker profile to select for a progeny plant with the desired trait and the molecular marker profile of year round flowering lupine.

Recurrent Selection and Mass Selection

Recurrent selection is a method used in a plant breeding program to improve a population of plants. Year round flowering lupine are suitable for use in a recurrent selection program. The method entails individual plants cross-pollinating with each other to form progeny. The progeny are grown and the superior progeny selected by any number of selection methods, which include individual plant, half-sib progeny, full-sib progeny, and selfed progeny. The selected progeny are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating plants. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Mutation Breeding

Mutation breeding is another method of introducing new traits into year round flowering lupine. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Vainstein, "Breeding for Ornamentals: Classical and Molecular Approaches," Kluwer Academic Publishers (2002). In addition, mutations created in other lupine plants may be used to produce a backcross conversion of year round flowering lupine that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the subject lupine plants are intended to be within the scope of the embodiments of the application.

Single-Gene Conversions

When the term lupine plant is used in the context of an embodiment of the present application, this also includes any single gene conversions of year round flowering lupine. The term single gene converted plant as used herein refers to those lupine plants which are developed by a plant breeding technique called backcrossing wherein essentially all of the desired morphological and physiological characteristics of a variety are recovered in addition to the single gene transferred into the variety via the backcrossing technique. Backcrossing methods can be used with one embodiment of the present application to improve or introduce a characteristic into the plant. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental lupine plant that contributes the gene for the desired characteristic is termed the nonrecurrent or donor parent. This terminology refers to the fact that the nonrecurrent parent is used one time in the backcross protocol and therefore does not recur. The parental lupine plant to which the gene or genes from the nonrecurrent parent are transferred is known as the recurrent parent as it is used for several rounds in the backcrossing protocol (Poehlman & Sleper (1994). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a lupine plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially important trait or traits to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. These traits are well-known in the art.

Introduction of a New Trait or Locus into Year Round Flowering Lupine

Year round flowering lupine represents a new base of genetics into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of Year Round Flowering Lupine

A backcross conversion of year round flowering lupine occurs when DNA sequences are introduced through backcrossing (Allard, "Principles of Plant Breeding" (1999) with year round flowering lupine utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, *Crop Science Society of America*, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. See, Allard, "Principles of Plant Breeding" (1999). Desired traits that may be transferred through backcross conversion include, but are not limited to, sterility (nuclear and cytoplasmic), fertility restoration, drought tolerance, nitrogen utilization, ornamental features, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments, the number of loci that may be backcrossed into year round flowering lupine is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes or genes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

In addition, the above process and other similar processes described herein may be used to produce first generation progeny lupine seed by adding a step at the end of the process that comprises crossing year round flowering lupine with the introgressed trait or locus with a different lupine plant and harvesting the resultant first generation progeny lupine seed.

Molecular Techniques Using Year Round Flowering Lupine

The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002).

Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing year round flowering lupine. See Vainstein, "Breeding for Ornamentals: Classical and Molecular Approaches," Kluwer Academic Publishers (2002).

Genetic Marker Profile Through SSR and First Generation Progeny

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs), all of which are well-known in the art.

Tissue Culture

Further reproduction of the variety can occur by tissue culture and regeneration. Tissue culture of various tissues of ornamental plants and lupine and regeneration of plants therefrom is well-known and widely published. For example, reference may be had to do Valla Rego, Luciana et al., *Crop Breeding and Applied Technology*. 1(3): 283-300 (2001); Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992). Thus, another embodiment is to provide cells which upon growth and differentiation produce lupine plants having the physiological and morphological characteristics of year round flowering lupine described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as pollen, ovules, embryos, protoplasts, meristematic cells, callus, pollen, leaves, ovules, anthers, cotyledons, hypocotyl, pistils, roots, root tips, flowers, seeds, petiole, pods, shoot, or stems, and the like. Means for preparing and maintaining plant tissue culture are well-known in the art.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope. The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice one or more embodiments.

Deposit Information

A representative sample of proprietary *Lupinus* polyphyllus hybrid seed comprising the lines described herein of the Green Fuse Botanicals, Inc., wherein said deposit is designated *Lupinus* sp. year round flowering and wherein said year round flowering lupine plants grown from said seed exhibit a year round flowering characteristic have been made with the National Collections of Industrial, Food and Marine Bacteria (NCIMB), Ferguson Building, Craibstone Estate, Bucksburn, Aberdeen, Scotland, AB21 9YA, United Kingdom. The date of deposit of 1,491 was Mar. 28, 2017 and the NCIMB No. is 42735. On Apr. 4, 2017, an additional supplemental deposit of 1,770 seeds was made with NCIMB. The deposit of at least 2,500 seeds was taken from the same deposit maintained by Green Fuse Botanicals, Inc. since prior to the filing date of this application. Upon issuance of a patent, all restrictions on the availability to the public of the deposit will be irrevocably removed consistent with all of the requirements of 37 C.F.R. §§ 1.801-1.809. The deposit will be maintained in the depository for a period of thirty years, or five years after the last request, or for the enforceable life of the patent, whichever is longer, and will be replaced as necessary during the period.

What is claimed is:

1. A *Lupinus polyphyllus* hybrid lupine plant comprising a year round flowering characteristic, wherein said year round flowering characteristic comprises a lupine plant which will initiate flowering without vernalization and in days of short photoperiods, and wherein said lupine plant is produced from a representative sample of seed, wherein seed from said representative sample has been deposited with the National Collections of Industrial, Food and Marine Bacteria under NCIMB Accession number 42735.

2. The lupine plant of claim 1, wherein said lupine plant is a tetraploid or diploid.

3. A lupine seed produced by growing the plant of claim 1.

4. A lupine plant, or a plant part thereof, produced by growing the seed of claim 3, wherein said plant comprises the year round flowering characteristic.

5. The plant part of claim 4, wherein the plant part comprises a cell, seed, embryo, protoplast, tissue culture, or vegetative cutting.

6. A tissue culture produced from protoplasts or cells from the plant of claim 1, wherein said cells or protoplasts are produced from a plant part selected from the group consisting of pollen, ovules, embryos, protoplasts, meristematic cells, callus, leaves, anthers, cotyledons, hypocotyl, pistils, roots, root tips, flowers, seeds, petiole, pods, and stems.

7. A lupine plant regenerated from the tissue culture of claim 6, wherein said plant comprises the year round flowering characteristic.

8. A method for producing lupine seed, said method comprising crossing two lupine plants and harvesting the resultant lupine seed, wherein at least one lupine plant is the lupine plant of claim 1.

9. A method for producing a lupine plant having a year round flowering characteristic, wherein the method comprises:
crossing two lupine parent plants and harvesting the resultant seed or embryo to produce $F_1$ progeny, wherein at least one parent plant is the *Lupinus polyphyllus* hybrid lupine of claim 1;
backcrossing said $F_1$ progeny to said parent having said year round flowering characteristic and harvesting the resultant $F_2$ seed or embryo; and
growing said $F_2$ progeny and selecting for plants having a year round flowering characteristic.

10. A lupine plant produced from the method of claim 9, wherein said plant has a year round flowering characteristic.

11. The method of claim 9, wherein said second parent plant is a lupine selected from the group consisting of *Lupinus polyphyllus, Lupinus arboreus, Lupinus sulphureus*, and *Lupinus nooktatensis*.

12. The method of claim 9, wherein said $F_1$ progeny is self-pollinated to produce an $F_2$ progeny having a year round flowering characteristic.

13. The method of claim 9, wherein said $F_1$ progeny is intercrossed to produce an $F_2$ progeny having a year round flowering characteristic.

14. The lupine plant of claim 1, wherein said lupine plant is a dwarf variety.

15. The lupine plant of claim 14, wherein the inflorescence of said lupine produces flowers that are blue, purple, white, red, pink, yellow, orange, or combinations and shades thereof.

16. The lupine plant of claim 1, wherein said lupine plant is a tall variety.

17. The lupine plant of claim 16, wherein the inflorescence of said lupine produces flowers that are blue, purple, white, red, pink, yellow, orange, or combinations and shades thereof.

\* \* \* \* \*

SEQUENCE LISTING

<160> NUMBER OF SEQ ID NOS: 4

<210> SEQ ID NO 1
<211> LENGTH: 121

```
<212> TYPE: DNA
<213> ORGANISM: Lupinus polyphyllus hybrid

<400> SEQUENCE: 1
ttagttttct tgaataaaaa agtgattttg acaatggatt aatgaaataa agtctaaagc      60
ttcaaattat atatacttaa atgctcaaat tgttgctgaa aatttgtgtt ttgaatttt     120 t                                                                    121

<210> SEQ ID NO 2
<211> LENGTH: 119
<212> TYPE: DNA
<213> ORGANISM: Lupinus polyphyllus hybrid

<400> SEQUENCE: 2
ttagttttct tgaataaaaa agtgattttg acaatggatt aatgaaataa agtctaaagc      60
ttcaaattat atatacttaa atgctcaaat tggctaaaaa tttgtgtttt gatttttt      119

<210> SEQ ID NO 3
<211> LENGTH: 25
<212> TYPE: DNA
<213> ORGANISM: Lupinus polyphyllus hybrid

<400> SEQUENCE: 3
cagtaaccct ttcttgaggg aatac                                           25

<210> SEQ ID NO 4
<211> LENGTH: 22
<212> TYPE: DNA
<213> ORGANISM: Lupinus polyphyllus hybrid

<400> SEQUENCE: 4
ccaaacactg cacttgtggt ag                                              22
```